United States Patent [19]

Baraldi

[11] Patent Number: 6,048,865
[45] Date of Patent: Apr. 11, 2000

[54] N⁶-SUBSTITUTED-ADENOSINE-5'-URONAMIDES AS ADENOSINE RECEPTOR MODULATOR

[75] Inventor: Pier Giovanni Baraldi, Ferrara, Italy

[73] Assignee: Medco Research, Inc., Research Triangle Park, N.C.

[21] Appl. No.: 09/124,434

[22] Filed: Jul. 29, 1998

Related U.S. Application Data

[60] Provisional application No. 60/055,064, Jul. 29, 1997.

[51] Int. Cl.⁷ .................................................. A01N 43/90
[52] U.S. Cl. ............................................ 514/266; 544/277
[58] Field of Search ............................. 544/277; 514/266

[56] References Cited

U.S. PATENT DOCUMENTS 5,310,731   5/1994   Olsson et al. .............................. 514/46

OTHER PUBLICATIONS

Abbracchio, M.P. et al., G Protein–Dependent Activation of Phospholipase C by Adenosine $A_3$ Receptors in Rat Brain, Mol. Pharmacol, vol. 48, No. 6, pp. 1038–1045 (1995).

Baraldi et al., Synthesis of new pyrazolo [4,3–e]–1,2,4–triazolo[1,5–c] pyrimidine and 1,2,3–triazolo[4,5–e] 1,2,4–triazolo [1,5–c]pyrimidine displaying potent and selective activity as $A_{2a}$ adenosine receptor antagonist, Bioorg. Med. Chem. Lett. vol. 4, pp. 2539–2544 (1994).

Baraldi et al., Current Developments of $A_{2a}$ Adenosine Receptor Antagonists, Current Medicinal Chemistry, vol. 2, pp. 707–722 (1995).

Gallo–Rodriguez, et al., Structure–Activity Relationship of N⁶–Benzyladenosine–5'–uronamides as $A_3$–Selective Adenosine Agonists, J. Med. Chem. vol. 37, pp. 636–646 (1994).

Jacobson, "Adenosine $A_3$ receptors: novel ligands and paradoxical effects," TIPS, vol. 19, pp. 185–191, (May 1998).

Jacobson, et al., Adenosine Receptors: Pharmacology, Structure–Activity Relationships, and Therapeutic Potential, J. Med. Chem. vol. 35, No. 3, pp. 407–422 (1992).

Jacobson, et al., Structure–Activity Relationships of 8–Styrylxanthines as $A_2$–Selective Adenosine Antagonists, J. Med. Chem, vol. 36, pp. 1333–1342 (1993).

Jacobson, et al., A role for central $A_3$–adenosine receptors: Mediation of behavioral depressant effects, FEBS Lett, vol. 336, pp. 57–60 (1993).

Jacobson, et al., $A_3$–adenosine receptors: design of selective ligands and therapeutic prospects, Drugs of the Future, vol. 20(7), pp. 689–699 (1995).

Jacobson, et al. Structure–Activity Relationships of 9–Alkyladenine and Ribose–Modified Adenosine Derivatives at Rat $A_3$ Adenosine Receptors, J. Med. Chem., vol. 38, pp. 1720–1735 (1995).

Jiang J. et al., 6–Phenyl–1,4–dihydropyridine Derivatives as Potent and Selective $A_3$ Adenosine Receptor Antagonists, J. Med. Chem., vol. 39, pp. 4667–4675 (1996).

Jiang J. et al., Structure–Activity Relationships of 4–(phenylethylnyl)–6–phenyl–1,4–dihydropyridines as Highly Selective $A_3$ Adenosine Receptor Antagonists, J. Med. Chem., vol. 40, pp. 2596–2608 (1997).

Karton, Y. et al., Synthesis and Biological Activities of Flavnoid Derivatives as $A_3$ Adenosine Receptor Antagonists, J. Med. Chem., vol. 39 pp. 2293–2301 (1996).

Kim, H.O. et al., 2–Substitution of N⁶–Benzyladenosine–5'–uronamides Enhances Selectivity for $A_3$ Adenosine Receptors, J. Med. Chem. vol. 37, pp. 3614–3621 (1994).

Kim, Y.C. et al., Derivatives of the Triazoloquinazoline Adenosine Antagonist Are Selective for the Human $A^3$ Receptor Subtype, J. Med. Chem., vol. 39 pp. 4142–4148 (1996).

Kohno et al., Induction of Apoptosis in HL–60 Human Promyelocytic Leukemia Cells by Adenosine $A_3$ Receptor Agonists, Biochm. Biophy. Res. Comm. V. 219, pp. 904–910 (1996).

Linden, J., Cloned adenosine $A_3$ receptors–pharmacological properties, species, differences and receptor functions, Trends Pharmacol, Sci., vol. 15, pp. 298–300 (1994).

Mathot et al., Deoxyribose analogues of N⁶–cyclopentyladenosine (CPA): partial agonists at the adenosine $A_1$ receptor in vivo, Brit J. Pharmacol, vol. 116, pp. 1957–1964 (1995).

Olah, M.E. et al., [$^{125}$I]1–4–Aminobenzyl5'–N–methylcarboxamidoadenosine, a High Affinity Radioligand for the Rat $A_3$ Adenosine Receptor, Mol. Pharm., vol. 45, pp. 978–982 (1994).

Siddiqi, S.M., et al., Comparative Molecular Field Analysis of Selective $A_3$ Adenosine Receptor Agonists, Bioorg. Med. Chem., vol. 3, pp. 1331–1343 (1995).

van Bergen A., et al., $A_3$ Receptors: Structure Activity Relationships and Molecular Modeling, ACS 206th National Meeting, Abstract MED217 (1993).

van Calenbergh, N⁶–Cyclopentyl–3'–substituted–xylofuranosyladenosines: A New Class of Non–Xanthine Adenosine $A_1$ Receptor Antagonists, J. Med. Chm, V40, p3765–3772 (1997).

(List continued on next page.)

*Primary Examiner*—Mukund J. Shah
*Assistant Examiner*—Ann M. Kessinger
*Attorney, Agent, or Firm*—Burns, Doane, Swecker & Mathis, L.L.P.

[57] ABSTRACT

A series of adenosine-5'-uronamide derivatives bearing N⁶-arylurea, alkarylurea, heteroarylurea, arylcarbonyl, alkarylcarbonyl or heteroarylcarbonyl groups which have affinity and, in some cases, selectivity for the adenosine $A_1$ or $A_3$ receptors are disclosed. These compounds can be used in a pharmaceutical composition to treat disorders caused by excessive activation of the $A_1$ or $A_3$ receptors, or can be used in a diagnostic application to determine the relative binding of other compounds to the $A_1$ or $A_3$ receptors.

15 Claims, 3 Drawing Sheets

OTHER PUBLICATIONS van Galen, P.J.M., et al., A Binding Site Model and Structure–Activity Relationships for the Rat $A_3$ Adenosine Receptor, Mol. Pharmacol, vol. 45, pp. 1101–1111 (1994).

van Rhee, et al., Interaction of 1,4–Dihydropyridine and Pyridine Derivatives with Adenosine Receptors: Selectively for $A_3$ Receptors, J. Med. Chem., vol. 39, pp. 2980–2989 (1996).

van Rhee, A.M. et a., Tetrahydrobenzothiophenone Derivatives as a Novel Class of Adenosine, J. Med. Chem., vol. 39, pp. 398–406 (1996).

von Lubitz, D.K.J.E., et al., Adenosine $A_3$ receptor stimulation and cerebal ischemia, Eur. J. Pharmacol, vol. 263, pp. 59–67 (1994).

Zhou, Q.Y. et al., Molecular cloning and characterization of an adenosine receptor:The $A_3$ adenosine receptor, Proc. Natl. Acad. Sci. USA, vol. 89, pp. 7432–7436 (1992).

Baraldi et al., "Novel N6–(Substituted–phenylcarbamoyl)adenosine–5;–uronamides as Potent Agonists for A3 Adenosine Receptors," J. Med. Chem., vol. 39, No. 3, pp. 802–806, Feb. 2, 1996.

Von Lubitz et al., "Adenosine A3 receptor stimulation and cerebral ischemia," Eur. J. Pharmacol., vol. 263, No. 1–2, pp. 59–67, MEDLINE abstract, Sep. 1994.

Stambaugh et al., "A novel cardioprotective function of adenosine A1 and A3 receptors during prolonged simulated ischemia," Am. J. Physiol., vol. 273, No. 1 Pt. 2, pp. 501–505, MEDLINE abstract, Jul. 1997.

Reeves et al., "Adenosine A3 receptors promote degranulation of rat mast cells both in vitro and in vivo," Inflamm. Res., vol. 46, No. 5, pp. 180–184, MEDLINE abstract, May 1997.

Keller, "Arteriolar constriction in skeletal muscle during vascular stunning: Role of Mast Cells," Am. J. Physiol., vol. 272, No. 5 Pt. 2), pp. 2154–2163, MEDLINE abstract, May 1997.

Monti et al., "p–SPA, a peripheral adenosine A1 analogue, reduces sleep apneas in rats," Pharmacol. Biochem. Behav., vol. 53, No. 2, pp. 341–345, MEDLINE abstract, Feb. 1996.

$N^6$-SUBSTITUTED-ADENOSINE-5'-URONAMIDES AS ADENOSINE RECEPTOR MODULATOR

This Application is a non-provisional application claiming priority to U.S. Provisional Patent Application No. 60/054,064, filed Jul. 29, 1997, herein incorporated by reference in its entirety.

FIELD OF THE INVENTION

The present invention relates to certain $N^6$-substituted-adenosine-5'-uronamide derivatives and their use in the practice of medicine as compounds with activity as agonists of adenosine receptors, in particular, the adenosine $A_1$ and $A_3$ receptors.

BACKGROUND OF THE INVENTION

Three major classes of adenosine receptors, classified as $A_1$, $A_2$, and $A_3$, have been characterized pharmacologically and have been defined on the basis of cloned sequences[1-4]. $A_1$ receptors are coupled to the inhibition of adenylate cyclase through $G_i$ proteins and have also been shown to couple to other secondary messenger systems, including inhibition or stimulation of phosphoinositol turnover and activation of ion channels. $A_2$ receptors are further divided into two subtypes, $A_{2A}$ and $A_{2B}$, at which adenosine agonists activate adenylate cyclase with high and low affinity, respectively. The $A_3$ receptor sequence was first identified in a rat testes cDNA library, and this sequence, later cloned by homology to other G-protein coupled receptors from a rat brain cDNA library, was shown to correspond to a novel, functional adenosine receptor.

Many selective agonists and antagonists have been developed for the $A_1$[10-15] and $A_{2a}$[16-19] receptor subtypes. Some of these have shown promise as potential therapeutic agents in the treatment of hypertension[17], Parkinson's disease[20], cognitive deficits[21], schizophrenia[22], epilepsy and renal failure[23]. Selective and/or high affinity agonists and antagonists for the $A_{2b}$ receptor are not well known.

The discovery of the $A_3$ receptor has opened new therapeutic vistas in the purine field. In particular, the $A_3$ receptor mediates processes of inflammation, hypotension, and mast cell degranulation. This receptor apparently also has a role in the central nervous system. The $A_3$ selective agonist IB-MECA induces behavioral depression and upon chronic administration protects against cerebral ischemia. $A_3$ selective agonists at high concentrations were also found to induce apoptosis in HL-60 human leukemia cells. These and other findings have made the $A_3$ receptor a promising therapeutic target. Selective antagonists for the $A_3$ receptor are sought as potential antiinflammatory or possibly antiischemic agents in the brain. Recently, $A_3$ antagonists have been under development as antiasthmatic, antidepressant, antiarrhythmic, renal protective, antiparkinson and cognitive enhancing drugs.

Selective agonist[24] and antagonist[25-28] ligands have been developed for the $A_3$ receptor. In the agonist field, 1B-MECA ($N^6$-(3-iodobenzyl)adenosine-5'-methyluronamide) shows a Ki value of 1.1 nM at rat $A_3$ receptors and a 50-fold selectivity versus either $A_1$ or A2a receptors[29]. The related agonist, [125I]AB-MECA ($N^6$-(4-amino-3-iodobenzyl)adenosine-5'-methyluronamide)[30] has become a useful radioligand for the screening of new derivatives at cloned $A_3$ receptors.

More recently, $N^6$-(substituted phenylcarbamoyl) adenosine-5'-uronamides, where the substituent is 2-chloro, 3-chloro or 4-methoxy, have been prepared (Baraldi et al., *Advance ACS Abstracts*, Dec. 15, 1995) and demonstrated affinity at $A_3$ receptors in the low nanomolar range (Ki values less than 10 nm). However, other closely related substituents, such as 3-bromo, showed a ten-fold loss in activity and affinity for the $A_3$ receptor (Baraldi et al., *J. Med Chem.*, 39:802–806 (1996). Further, while the 2-chloro, 3-chloro and 4-methoxy substituents showed high affinity for the $A_3$ receptor and high selectivity relative to the $A_2$ receptor, the selectivity for the $A_1$ receptor was not as high (the ratio of $A_3$ to $A_1$ activity was between 4 and 15).

A number of $A_3$ adenosine receptor agonists which have been previously synthesized are structurally related to adenosine itself, in which the ribose moiety is mainly intact. On the ribose, 5'-alkyluronamide groups are generally tolerated. Positions on the structure of adenosine providing flexibility of substitution, in general for adenosine agonists, have been the $N^6$ and $C_2$ position. At the $N^6$ position, most alkyl or aryl derivatives are $A_1$ selective. At the $C_2$ position, many C-, N-, or O-derivatives are $A_{2a}$ selective. Benzyl derivatives at the $N^6$ position have been shown to be $A_3$ selective.

It would be advantageous to provide other modulators of the $A_1$ and $A_3$ receptors, with high affinity and selectivity for these receptors with respect to the other adenosine receptors.

It is therefore an object of the present invention to provide compounds and methods of preparation and use thereof, which are agonists or partial agonists of the adenosine receptors, in particular, the adenosine $A_1$ and $A_3$ receptors.

SUMMARY OF THE INVENTION

Compounds useful as potent, and in some cases, selective agonists of the adenosine $A_1$ and $A_3$ receptors, and methods of preparation and use thereof, are disclosed.

The compounds have the following general formula:

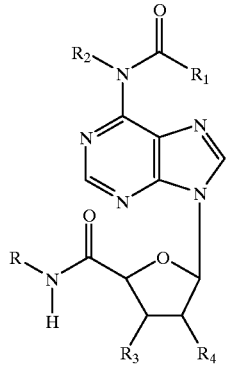

wherein:
R is hydrogen, alkyl, substituted alkyl, or aryl;
$R^1$ is heteroaryl-NR—, heteroaryl- or aryl
$R^2$ is hydrogen, alkyl, substituted alkyl, or aryl-NH—C(X)—, and
X is O, S, or NR, with the proviso that, when $R^2$ is H, $R^1$ is aryl-NH—C(X)— and X is O, the substituents on the aryl ring are not halo, methoxy or trifluoromethyl.
$R^3$ and $R^4$ are, independently selected from the group consisting of halo, ether, ester, azide, alkyl, alkoxy, carboxy, nitrile, nitro, aryl, alkaryl, thio, thioester, thioether, amine, amide and other substituents routinely used in the field of nucleoside chemistry to modify these positions. Such modifications are expected to provide the compounds with activity as partial agonists.

When $R^1$ is heteroaryl-NR—, heteroaryl-, or aryl-, the compounds tend to show affinity, and, in some cases, selectivity for the adenosine $A_1$ receptor. When $R^1$ is alkaryl-NR—C(X)—, substituted alkaryl-NR—C(X)—, or aryl-NR—C(X)—, the compounds tend to show affinity and selectivity for the $A_3$ receptor. Preferred substituents include p-sulfonamide, p-nitro, p-phenyl, 2,4-dichloro, p-methoxy, m-chloro, o-chloro and p-nitro.

The compounds can be used in a method for fully or partially inhibiting adenylate cyclase ($A_1$ and $A_3$) in a mammal, including a human. The methods involve administering an effective amount of a compound of formula I sufficient to fully or partially inhibiting adenylate cyclase in the mammal.

Additionally, the compounds can be used in competitive binding assays to determine the activity of other compounds in their ability to bind the $A_1$ or $A_3$ receptor.

The compounds can be used in a pharmaceutical formulation that includes a compound of formula I and one or more excipients. Various chemical intermediates, such as 2',3-isopropylidene-N-alkylcarboxamido adenosines, can be used to prepare the compounds.

DETAILED DESCRIPTION OF THE INVENTION

Figure 1:
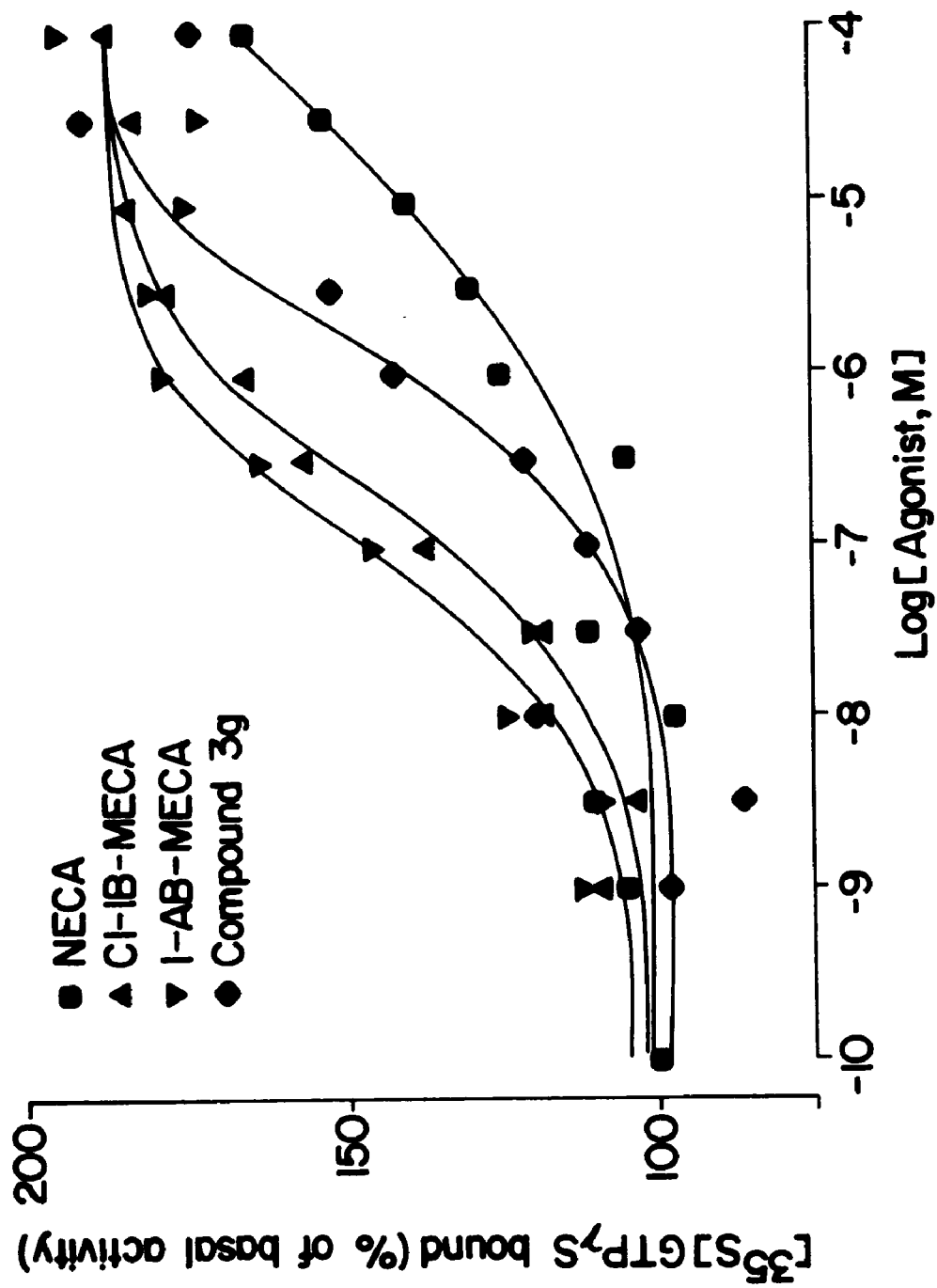
FIG. 1 is a graph showing the effect of various adenosine agonists, 5'-(N-ethylcarboxamido)adenosine (NECA), $N^6$-sulfonamidophenylcarbamoyl)adenosine-5'-N-ethyluronamide, 2-chloro-$N^6$-(3-iodobenzyl)adenosine-5'-N-methyluronamide (Cl-IB-MECA), and $N^6$-(4-amino-3-iodobenzyl)adenosine-5'N-methyluronamide (I-AB-MECA) on the binding of [$^{35}$S]GTP-γ-S to membranes of RBL-2H3 rat mast cells.

The present application discloses compounds useful as agonists or partial agonists of adenosine receptors, in particular, with activity as $A_1$ or $A_3$ agonists or partial agonists, and methods of preparation and use thereof.

The compounds can be used in a method for treating a mammal, including a human, with excessive activity at adenosine receptors, in particular, $A_1$ or $A_3$ receptors. The methods involve administering to the mammal an effective amount of a compound of formula I sufficient to modulate adenosine receptors in the mammal. The compounds can be used in a pharmaceutical formulation that includes a compound of formula I and one or more excipients.

Definitions

As used herein, a compound is an agonist of an adenosine $A_1$ or $A_3$ receptor if it is able to fully inhibit adenylate cyclase ($A_1$ and $A_3$) and is able to displace [$^{125}$I]-AB-MECA in a competitive binding assay.

As used herein, a compound is a partial agonist of an adenosine $A_1$ or $A_3$ receptor if it is able to partially inhibit adenylate cyclase ($A_1$ and $A_3$) and is able to displace [$^{125}$I]-AB-MECA in a competitive binding assay.

As used herein, a compound is an antagonist of an adenosine $A_1$ or $A_3$ receptor if it is able to prevent the inhibition due to an agonist and is able to displace [$^{125}$I]-AB-MECA in a competitive binding assay.

As used herein, a compound is selective for the $A_1$ receptor if the ratio of $A_2/A_1$ and $A_3/A_1$ activity is greater than about 50, preferably between 50 and 100, and more preferably, greater than about 100. A compound is selective for the $A_3$ receptor if the ratio of $A_1/A_3$ and $A_2/A_3$ activity is greater than about 50, preferably between 50 and 100, and more preferably, greater than about 100.

As used herein, the term "alkyl" refers to monovalent straight, branched or cyclic alkyl groups preferably having from 1 to 20 carbon atoms, more preferably 1 to 10 carbon atoms ("lower alkyl") and most preferably 1 to 6 carbon atoms. This term is exemplified by groups such as methyl, ethyl, n-propyl, iso-propyl, n-butyl, iso-butyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, cyano, halogen, hydroxyl, carboxyl, carboxylalkyl, thiol, thioalkoxy, substituted thioalkoxy, aryl, aryloxy, heteroaryl, heteroaryloxy, hydroxylamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl) amino, mono- and di-arylamino, mono- and di-heteroarylamino, and unsymmetric di-substituted amines having different substituents selected from alkyl, aryl, and heteroaryl. As used herein, other moieties having the prefix "substituted" are intended to include one or more of the substituents listed above.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl-C(O)—, cycloalkyl-C(O)—, substituted cycloalkyl-C(O)—, aryl-C(O)—, and heteroaryl-C(O)— where alkyl, substituted alkyl, cycloalkyl, substituted cycloalkyl, aryl, and heteroaryl are as defined herein.

As used herein, the term "acylamino" refers to the group —C(O)NRR where each R is independently hydrogen, alkyl, substituted alkyl, aryl, or heteroaryl wherein alkyl, substituted alkyl, aryl and heteroaryl are as defined herein.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, alkaryl, aryl, aryloxy, azido, carboxyl, carboxylalkyl, cyano, halo, nitro, heteroaryl, heteroaryloxy, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, aryl, aryloxy, azido, carboxyl, carboxylalkyl, cyano, halo, nitro, heteroaryl, heteroaryloxy, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

As to any of the above groups that contain 1 or more substituents, it is understood, of course, that such groups do not contain any substitution or substitution patterns which are sterically impractical and/or synthetically non-feasible.

"Pharmaceutically acceptable salts" refers to pharmaceutically acceptable salts of a compound of Formula I, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

The following abbreviations are used herein: Abbreviations: [$^{125}$I]AB-MECA, [$^{125}$I]N$^6$-(4-amino-3-iodobenzyl) adenosine-5'N-methyluronamide; CHO cells, Chinese hamster ovary cells; CGS 21680, 2-[4-[(2-carboxyethyl)phenyl] ethyl-amino]-5'-N-ethylcarboxamido adenosine; Cl-IB-MECA, 2-chloro-N$^6$-(3-iodobenzyl)adenosine-5'-N-methyluronamide; (R)-PIA, (R)-N$^6$-(phenylisopropyl) adenosine; DMSO, dimethysulfoxide; EDTA, ethylenediamine tetraacetic acid, I-AB-MECA, N$^6$-(4-amino-3-iodobenzyl)adenosine-5'-N-methyluronamide; IB-MECA, N$^6$-(3-iodobenzyl)adenosine-5'-N-methyluronamide; Ki, equilibrium inhibition constant; NECA, 5'-N-ethylcarboxamido adenosine; THF, tetrahydrofuran; Tris, tris(hydroxymethyl)aminomethane.

Compound Preparation

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amine group converted to an amide or carbamate. Methods of protecting and de-protecting, also known as "blocking" and "de-blocking," are well known and widely practiced in the art, e.g., see T. Green, *Protective Groups in Organic Synthesis*, John Wiley, New York (1981) or *Protective Groups in Organic Chemistry*, Ed. J. F. W. McOmie, Plenum Press, London (1973).

The compounds can be prepared as described below. Generally, the 2'- and 3'-hydroxy groups on an N-alkyl carboxamido adenosine, such as 5'-(N-ethylcarboxamido) adenosine (NECA), are protected. A suitable protecting group is an isopropylidene ring, although other protecting groups can be used and are intended to be within the scope of the invention.

Figure 2A:
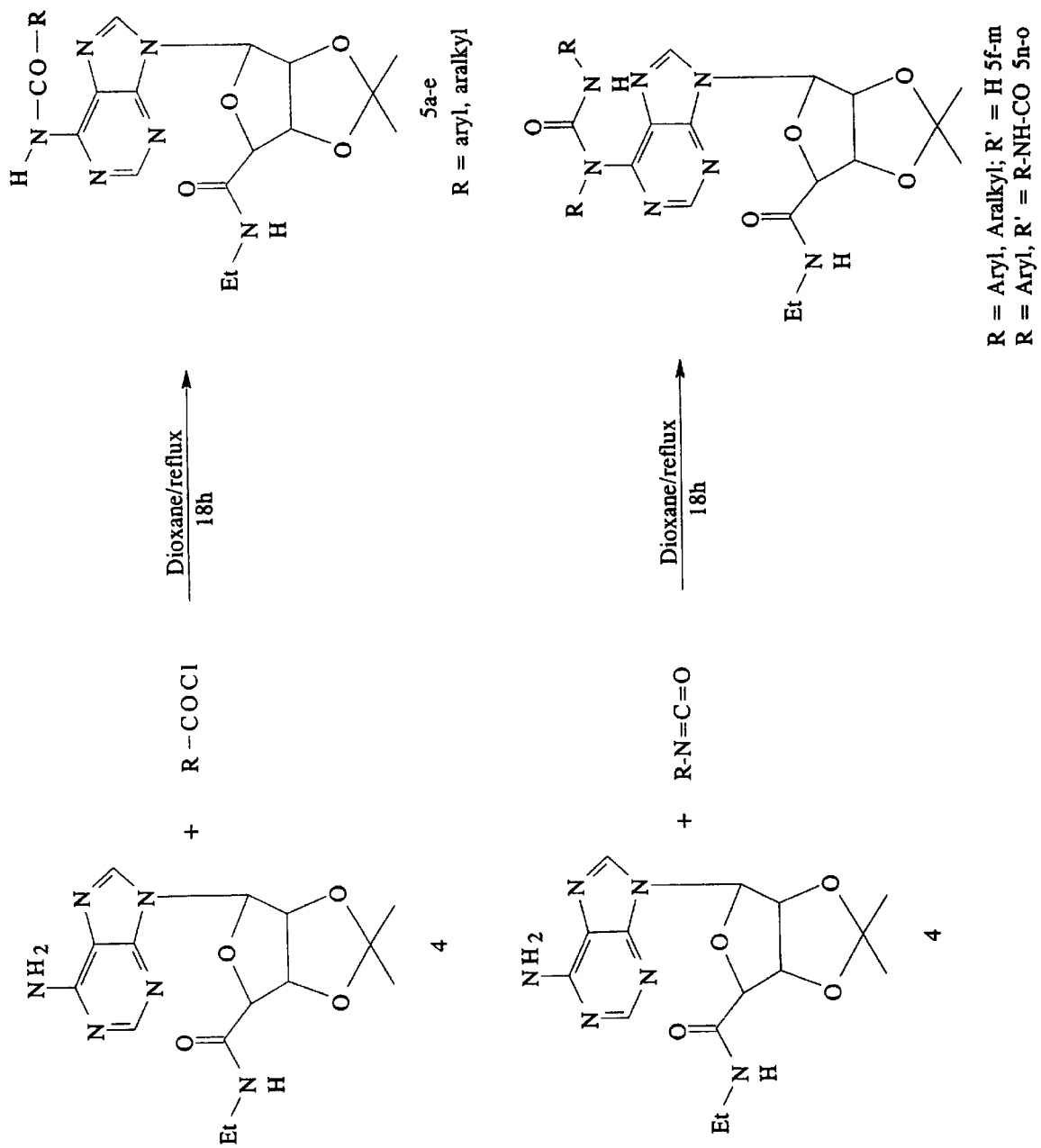
FIGS. 2a and 2b are reaction schemes for preparing compounds of formula I.
Figure 2B:
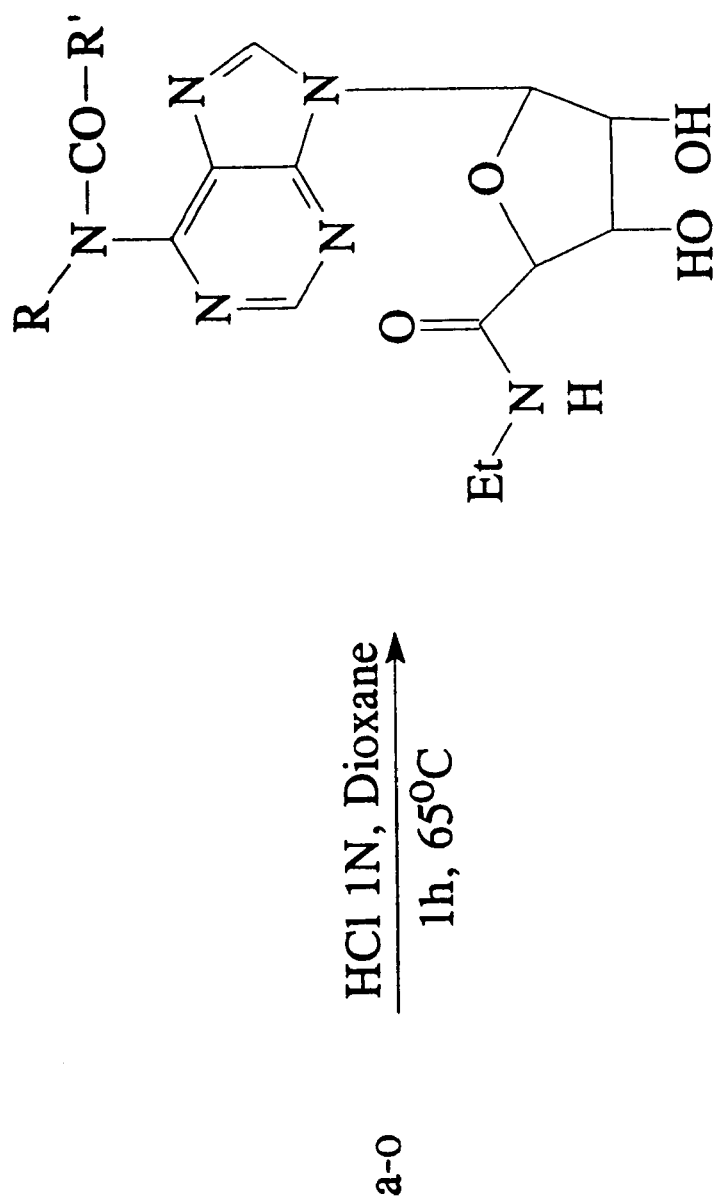

2',3'-O-isopropylidene-N$^6$-(substituted-carbonylamino)-adenosine-5'-alkyluronamides can be prepared from the isopropylidene protected N-alkylcarboxamido adenosines by reaction of the N$^6$-amine group with an appropriate acid chloride or other suitable activated carboxylic acid derivative, such as an anhydride, using routine amidation conditions (as shown in FIG. 2a). 2',3'-O-isopropylidene-N$^6$-(substituted-carbamoylamino)-adenosine-5'-alkyluronamides can be prepared from the isopropylidene protected N-alkylcarboxamido adenosines by reaction of the N$^6$-amine group with an appropriate isocyanate using known chemistry (as shown in FIG. 2b). The protecting groups are then removed to provide the desired compounds.

In those embodiments in which the 2' and/or 3'-hydroxy groups have been replaced with halo, ether, ester, azide, alkyl, alkoxy, carboxy, nitrile, nitro, aryl, alkaryl, thio, thioester, thioether, amine, or amide groups, the chemistry proceeds in substantially the same manner, except that thio and amine groups, which would interfere with the coupling chemistry, must first be protected with suitable protecting groups prior to coupling the N$^6$ amine group with an acid halide or isocyanate.

Methods of Using the Compounds

The compounds can be used for all indications for which agonists and antagonists of the A$_1$ or A$_3$ receptor are effective.

Compounds which effectively modulate the $A_1$ receptor can be used for:

Protection against hypoxia and/or ischemia induced injuries (e.g., stroke, infarction);

Treatment of adenosine-sensitive cardiac arrhythmias;

antinociception (i.e., analgesics);

anticonvulsants;

cardioprotection, short term (e.g., prior to percutaneous angioplasty (PTDA), angioplasty, and cardiac surgeries) and long term (prevention of myocardial infarction, especially in high risk patients, reduction of infarct damage, especially in high risk patients);

neuroprotection: stroke prevention, stroke treatment, and the treatment of epilepsy;

pain management generally, including different forms of neuropathic pain, e.g., diabetic neuropathy, post herpetic neuralgia;

antilipid uses: reduction of free fatty acids, triglycerides, glucose;

adjunct therapy in diabetes, including insulin and non-insulin dependent diabetes mellitus: stimulation of insulin secretion from the pancreas, increase in tissue sensitivity to insulin;

treatment of GI disorders such as diarrhea, irritable bowel disease, irritable bowel syndrome, incontinence;

treatment of glaucoma;

treatment of sleep apnea;

treatment of cardiac disarrythmias (peroxysmal supraventricular tachycardia;

use in combination with anesthesia for post surgical pain;

treatment of inflammation;

diagnostic uses, for example, to determine the presence of one or more of the above described medical conditions, or in a screening assay to determine the effectiveness of other compounds for binding to the $A_1$ Ado receptor (i.e., through competitive inhibition as determined by various binding assays), as described in Jacobson and Van Rhee, Purinergic approaches to experimental therapy, Jacobson and Jarvis, ed., Wiley, New York, 1997, pp. 101–128; Mathot et al., *Brit. J. Pharmacol.*, 116:1957–1964 (1995); van der Wenden et al., *J. Med. Chem.*, 38:4000–4006 (1995); and van Calenbergh, *J. Med. Chem.*, 40:3765–3772 (1997), the contents of which are hereby incorporated by reference.

Compounds which effectively modulate the $A_3$ receptor can be used for:

treating hypertension;

mast cell degranulation;

antitumor agents;

treating cardiac hypoxia; and protection against cerebral ischemia;

as described, for example, in Jacobson, TIPS May 1998, pp. 185–191, the contents of which are hereby incorporated by reference.

The compounds can be administered via any medically acceptable means. Suitable means of administration include oral, rectal, topical or parenteral (including subcutaneous, intramuscular and intravenous) administration, although oral or parenteral administration are preferred.

The amount of the compound required to be effective as agonist or partial agonist of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 µg/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dosage range would be about 75 mg to about 220 mg per day, and a typical dose would be about 150 mg per day. If discrete multiple doses are indicated, treatment might typically be 50 mg of a compound given 3 times per day.

Formulations

The compounds described above are preferably administered in a formulation including an active compound, i.e., a compound of formula I, together with an acceptable carrier for the mode of administration. Suitable pharmaceutically acceptable carriers are known to those of skill in the art.

The compositions can optionally include other therapeutically active ingredients such as antivirals, antitumor agents, antibacterials, anti-inflammatories, analgesics, and immunosuppresants. The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration include sterile aqueous preparations of the active compound, which are preferably isotonic with the blood of the recipient. Such formulations may contain distilled water, 5% dextrose in distilled water or saline. Suitable formulations also include concentrated solutions or solids containing the compound of formula (I) which upon dilution with an appropriate solvent give a solution suitable for parental administration.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

The compounds can also be administered locally by topical application of a solution, ointment, cream, gel, lotion or polymeric material (for example, a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds

The activity of the compounds can be readily determined using no more than routine experimentation using, for example, any of the following assays.

Rat $A_1$ and $A_{2A}$ Adenosine Receptor Binding Assay
Membrane Preparations

Male Wistar rats (200–250 g) can be decapitated and the whole brain (minus brainstem, striatum and cerebellum) was dissected on ice. The brain tissues can be disrupted in a Polytron (setting 5) in 20 vols of 50 mM Tris HCl, pH 7.4. The homogenate can then be centrifuged at 48,000 g for 10 min and the pellet resuspended in Tris-HCl containing 2 IU/ml adenosine deaminase, type VI (Sigma Chemical Company, St. Louis, Mo., U.S.A.). After a 30 min incubation at 37° C., the membranes can be centrifuged and the pellets stored at −70° C. Striatal tissues can be homogenized with a Polytron in 25 vol of 50 mM Tris HCl buffer containing 10 mM $MgCl_2$ pH 7.4. The homogenate can be centrifuged at 48,000 g for 10 min at 4° C. and resuspended in Tris HCl buffer containing 2 IU/ml adenosine deaminase. After a 30 min incubation at 37° C., the membranes can be centrifuged and the pellet stored at −70° C.

Radioligand Binding Assays

Binding of [$^3$H]-DPCPX (1,3-dipropyl-8-cyclopentylxanthine) to rat brain membranes can be performed essentially according to the method previously described by Bruns et al., *Proc. Natl. Acad, Sci. U.S.A.*, 77:5547–5551 (1980), the contents of which are hereby incorporated by reference. In this method, displacement experiments are performed in 0.25 ml of buffer containing 1 nM [$^3$H]-DPCPX, 100 µl of diluted membranes of rat brain (100 µg of protein/assay) and at least 6–8 different concentrations of examined compounds. Non specific binding is determined in the presence of 10 µM of CHA ($N^6$cyclohexyladenosine) and this is always ≦10% of the total binding. The incubation time is typically around 120 min at 25° C.

Bound and free radioactivity can be separated by filtering the assay mixture through Whatman GF/B glass-fiber filters, using a Brandel cell harvester (Gaithersburg, Md., U.S.A.). The incubation mixture is diluted with 3 ml of ice-cold incubation buffer, rapidly vacuum filtered and the filter is washed three times with 3 ml of incubation buffer. The filter bound radioactivity can be measured by liquid scintillation spectrometry. The protein concentration can be determined using known methodology, for example, using bovine albumin as a reference standard.

Human Cloned $A_3$ Adenosine Receptor Binding Assay
Receptor Binding Assays

Binding assays can be carried out according to the method described by Salvatore et al., *Proc. Natl. Acad. Sci. U.S.A.*, 90:10365–10369 (1993), the contents of which are hereby incorporated by reference. In saturation studies using this method, an aliquot of membranes (8 mg protein/ml) from HEK-293 cells transfected with the human recombinant $A_3$ adenosine receptor (Research Biochemical International, Natick, Mass., U.S.A.) are incubated with from 10 to 12 different concentrations of [$^{125}$I]AB-MECA ranging from 0.1 to 5 nM. Competition experiments are carried out in duplicate in a final volume of 100 µl in test tubes containing 0.3 nM [$^{125}$I]AB-MECA, 50 mM Tris HCl buffer, 10 mM $MgCl_2$, pH 7.4 and 20 µl of diluted membranes (12.4 mg protein/ml) and at least 6 to 8 different concentrations of examined ligands. Incubation time is typically around 60 min at 37° C.

Bound and free radioactivity are separated by filtering the assay mixture through Whatman GF/B glass-fiber filters using a Brandel cell harvester. Non-specific binding is defined as binding in the presence of 50 µM R-PIA and can be as high as about 30%. The incubation mixture is diluted with 3 ml of ice-cold incubation buffer, rapidly vacuum filtered and the filter is washed three times with 3 ml of incubation buffer. The filter bound radioactivity is counted in a Beckman gamma 5500B γ counter. The protein concentration can be determined according to known methodology, for example, using bovine albumin as reference standard.

Another suitable method for performing binding studies is the method reported in Baraldi et al., *J. Med. Chem.,* 39:802–806 (1996).

Data Analysis

Inhibitory binding constant ($K_i$) values were calculated from those of $IC_{50}$ according to Cheng & Prusoff equation (Cheng and Prusoff, *Biochem. Pharmacol.,* 22:3099–3108 (1973), the contents of which are hereby incorporated by reference), $K_i=IC_{50}/(1+[C^*]/K_D^*)$, where $[C^*]$ is the concentration of the radioligand and $K_D^*$ is its dissociation constant.

A weighted non linear least-squares curve fitting program, for example, LIGAND can be used for computer analysis of saturation and inhibition experiments. Data are typically expressed as geometric mean, with 95% or 99% confidence limits in parentheses.

Pharmacology

All synthesized compounds have been tested for their affinity at rat $A_1$ and $A_{2A}$ and human $A_3$ receptors.

EXAMPLES

The following examples illustrate aspects of this invention but should not be construed as limitations. The symbols and conventions used in these examples are intended to be consistent with those used in the contemporary, international, chemical literature, for example, the *Journal of the American Chemical Society* ("*J. Am. Chem. Soc.*") and *Tetrahedron.*

Experimental Section

Chemistry: Reactions were routinely monitored by thin-layer chromatography (TLC) on silica gel (precoated F254 Merck plates) and products visualized with iodine or aqueous potassium permanganate. Infrared spectra (IR) were measured on a Perkin Elmer 257 instrument. $^1$H NMR were determined in $CDCl_3$ or DMSO-d6 solutions with a Bruker AC 200 Spectrometer, with peak positions given in parts per million ($\delta$) downfield from tetramethylsilane as internal standard, and J values are given in Hz. Light petroleum ether refers to the fractions boiling at 46–60° C. Melting points were determined on a Buchi-Tuttoli instrument and are uncorrected. Chromatography was performed with Merck 60–200 mesh silica gel. All products reported showed IR and $^1$H NMR spectra in agreement with the assigned structures. Organic solutions were dried over anhydrous magnesium sulfate. Elemental analyses were performed by the microanalytical laboratory of Dipartimento di Chemica, University of Ferrara, and were within 0.4% of the theoretical values for C, H and N.

Example 1

General procedure for the preparation of 2',3'-O-isopropylidene-N$^6$-(substituted-carbonylamino)adenosine-5'-N-ethyluronamide 2',3'-isopropylidene-NECA (0.43 mmol) was dissolved in freshly distilled dioxane (4 ml) and the appropriate acid chloride (1.3 eq.) and a catalytic amount of triethylamine (2–3 drops) were added. The mixture was refluxed under argon for 15 hours. The solvent was then removed under reduced pressure and the residue was purified by flash chromatography ($CH_2Cl_2$-EtOAc 20%) to afford the desired compounds.

Example 2

Preparation of 2',3'-O-isopropylidene-N$^6$-(4-biphenyl-carbonylamino)adenosine-5'-N-ethyluronamide Following the procedure outlined in Example 1, the title compound was prepared in an 80% yield as a pale yellow foam. IR (neat) cm$^{-1}$ 3445, 1720, 1640, 1575; $^1$H NMR (CDCl$_3$) $\delta$: 0.84 (t, 3H, J=7); 1.39 (s, 3H); 1.62 (s, 3H); 3.02–3.11 (m, 2H); 4.71 (d, 1H, J=2); 5.39–5.46 (m, 2H); 6.19 (d, 1H, J=2); 6.66 (t, 1H, J=2); 7.40–7.74 (m, 7H); 8.09–8.16 (m, 3H); 8.74 (s, 1H); 9.44 (bs, 1H). Anal. ($C_{28}H_{28}N_6O_5$) Calc'd.: C, 63.63; H, 5.34, N, 15.90. Found: C, 63.80; H, 5.37, N, 15.82.

Example 3

Preparation of 2',3'-O-isopropylidene-N$^6$-(2,4-dichlorobenzyl-carbonylamino)adenosine-5'-N-ethyluronamide Following the procedure outlined in Example 1, the title compound was prepared in an 67% yield as a white foam. IR (neat) cm$^{-1}$ 3440, 1730, 1625, 1565, 1210; $^1$H NMR (CDCl$_3$) $\delta$: 0.82 (t, 3H, J=7); 1.17 (s, 3H); 1.26 (s, 3H); 2.99–3.13 (m, 2H); 4.32 (s, 2H); 4.72 (d, 1H, J=1.8); 5.38–5.48 (m, 2H); 6.16 (d, 1H, J=1.8); 6.56 (t, 1H, J=2); 7.20–7.32 (m, 3H); 7.41 (s, 1H); 8.20 (s, 1H); 8.67 (s, 1H); Anal. ($C_{23}H_{24}N_7O_5Cl_2$) Calc'd.: C, 57.73; H, 5.06, N, 20.49. Found: C, 57.62; H, 4.99, N, 20.42.

Example 4

Preparation of 2',3'-O-isopropylidene-N$^6$-(4-methoxyphenyl-carbonylamino)adenosine-5'-N-ethyluronamide Following the procedure outlined in Example 1, the title compound was prepared in an 85% yield as a white solid. IR (neat) cm$^{-1}$ 3445, 1715, 1640, 1555, 1210; $^1$H NMR (CDCl$_3$) $\delta$: 0.85 (t, 3H, J=7); 1.40 (s, 3H); 1.63 (s, 3H); 3.03–3.12 (m, 2H); 3.90 (s, 3H); 4.72 (d, 1H, J=2); 5.41–5.49 (m, 2H); 6.16 (d, 1H, J=2); 6.61 (t, 1H, J=2); 7.01 (d, 2H, J=9); 8.02 (s, 2H, J=9); 8.10 (s, 1H); 8.74 (s, 1H); 9.09 (bs, 1H). Anal. ($C_{23}H_{26}N_6O_6$) Calc'd.: C, 57.26; H, 5.43, N, 17.42. Found: C, 57.15; H, 5.35, N, 17.28.

Example 5

Preparation of 2',3'-O-isopropylidene-N$^6$-(2-chlorophenyl-carbonylamino)adenosine-5'-N-ethyluronamide Following the procedure outlined in Example 1, the title compound was prepared in an 72% yield as a white foam. IR (neat) cm$^{-1}$ 3435, 1720, 1620, 1550, 1230; $^1$H NMR (CDCl$_3$) $\delta$: 0.83 (t, 3H, J=7); 1.39 (s, 3H); 1.62 (s, 3H); 3.00–3.07 (m, 2H); 4.71 (d, 1H, J=2); 5.41–5.44 (m, 2H); 6.18 (d, 1H, J=2); 6.67 (t, 1H, J=2); 7.30–7.44 (m, 3H); 7.71–7.76 (m, 1H); 8.16 (s, 1H); 8.69 (s, 1H); 10.24 (bs, 1H). Anal. ($C_{22}H_{23}N_7O_5Cl$) Calc'd.: C, 52.75; H, 4.63, N, 19.57. Found: C, 52.59; H, 4.58, N, 19.43.

Example 6

Preparation of 2',3'-O-isopropylidene-N$^6$-(phenyl-carbonylamino)adenosine-5'-N-ethyluronamide Following the procedure outlined in Example 1, the title compound was prepared in an 90% yield as a pale yellow foam. IR (neat) cm$^{-1}$ 3425, 1730, 1640, 1555, 1240; $^1$H NMR (CDCl$_3$) $\delta$: 0.79 (t, 3H, J=7); 1.39 (s, 3H); 1.61 (s, 3H); 2.91–3.03 (m, 2H); 4.71 (d, 1H, J=2); 5.45–5.52 (m, 2H); 6.18 (d, 1H, J=2); 6.40 (t, 1H, J=2); 7.27–7.53 (m, 3H); 7.83–7.87 (m, 2H); 8.19 (s, 1H); 8.63 (s, 1H); 9.18 (bs, 1H). Anal. ($C_{22}H_{24}N_6O_5$) Calc'd.: C, 58.40; H, 5.35, N, 18.57. Found: C, 58.23; H, 5.28, N, 18.45.

Example 7

General procedure for the preparation of 2',3'-O-isopropylidene-N⁶-(substituted-carbamoylamino)adenosine-5'-N-ethyluronamide 2',3'-isopropylidene-NECA (0.43 mmol) was dissolved in freshly distilled THF (4 ml) and the appropriate isocyanate (1.3 eq.) and a catalytic amount of triethylamine (two drops) were added. The mixture was refluxed under argon for 18 hours. The solvent was then removed under reduced pressure and the residue was purified by flash chromatography ($CH_2Cl_2$-EtOAc 20%) to afford the desired compounds.

Example 8

Preparation of 2',3'-O-isopropylidene-N⁶-(benzyl carbamoylamino)adenosine-5'-N-ethyluronamide Following the procedure outlined in Example 7, the title compound was prepared in an 82% yield as a white solid, mp 109–111° C. IR (KBr) $cm^{-1}$ 3440, 1740, 1610, 1550, 1210; $^1$H NMR (CDCl$_3$) δ: 0.76 (t, 3H, J=7); 1.21 (s, 3H); 1.63 (s, 3H); 2.96–3.03 (m, 2H); 4.64 (d, 1H, J=6); 4.71 (d, 1H, J=1.8); 5.44–5.48 (m, 2H); 6.16 (d, 1H, J=2); 6.52 (t, 1H, J=2); 7.26–7.38 (m, 5H); 8.14 (s, 1H); 8.45 (s, 1H); 8.46 (s, 1H), 9.79 (bs, 1H). Anal. ($C_{26}H_{31}N_7O_5$) Calc'd.: C, 59.87; H, 5.99, N, 18.80. Found: C, 60.00; H, 6.03, N, 18.88.

Example 9

Preparation of 2',3'-O-isopropylidene-N⁶-(4-sulfonamido-phenylcarbamoylamino)adenosine-5'-N-ethyluronamide Following the procedure outlined in Example 7, the title compound was prepared in an 60% yield as a white solid, mp 207° C. IR (KBr) $cm^{-1}$ 3450–3250, 1730, 1610, 1565, 1360, 1230; $^1$H NMR (CDCl$_3$) δ: 0.57 (t, 3H, J=7); 1.35 (s, 3H); 1.54 (s, 3H); 2.96–3.03 (m, 2H); 4.60 (d, 1H, J=2); 5.47–5.50 (m, 2H); 6.47 (d, 1H, J=2); 6.60 (t, 1H, J=2); 7.26 (d, 2H, J=9); 7.74 (d, 2H, J=9); 8.60 (s, 1H); 8.64 (s, 1H), 9.22 (s, 1H); 10.47 (bs, 1H); 12.05 (s, 1H). Anal. ($C_{22}H_{26}N_8O_7S$) Calc'd.: C, 48.35; H, 4.79, N, 20.50. Found: C, 48.27; H, 4.79, N, 20.63.

Example 10

Preparation of 2',3'-O-isopropylidene-N⁶-(4-acetyl-phenylcarbamoylamino)adenosine-5'-N-ethyluronamide Following the procedure outlined in Example 7, the title compound was prepared in an 77% yield as a white solid, mp 204° C. IR (KBr) $cm^{-1}$ 3430, 1740, 1720, 1630, 1545, 1240; $^1$H NMR (CDCl$_3$) δ: 0.83 (t, 3H, J=7); 1.42 (s, 3H); 1.64 (s, 3H); 2.61(s, 3H); 2.99–3.08 (m, 2H); 4.74 (d, 1H, J=2); 5.47–5.55 (m, 2H); 6.21 (d, 1H, J=2); 6.47 (t, 1H, J=2); 7.74 (d, 2H, J=9); 7.98 (d, 2H, J=9); 8.21 (s, 1H); 8.63 (s, 1H), 8.67 (bs, 1H); 12.01 (s, 1H). Anal. ($C_{22}H_{26}N_8O_7$) Calc'd.: C, 51.36; H, 5.09, N, 21.78. Found: C, 51.35; H, 5.12, N, 21.66.

Example 11

Preparation of 2',3'-O-isopropylidene-N⁶-((R)-α-phenylethyl-carbamoylamino)adenosine-5'-N-ethyluronamide Following the procedure outlined in Example 7, the title compound was prepared in an 65% yield as a white solid, mp 110–111° C. IR (KBr) $cm^{-1}$ 3430, 1730, 1620, 1555, 1230; $^1$H NMR (CDCl$_3$) δ: 0.68 (t, 3H, J=7); 1.41 (s, 3H); 1.63 (s, 3H); 1.64 (d, 3H, J=7); 2.87–2.96 (m, 2H); 4.71 (d, 1H, J=1.8); 5.16 (m, 1H); 5.48–5.51 (m, 2H); 6.16 (d, 1H, J=2); 6.52 (bs, 1H); 7.25–7.408 (m, 5H); 8.15 (s, 1H); 8.51 (s, 1H); 9.84 (bs, 1H), 10.94 (s, 1H). Anal. ($C_{23}H_{29}N_7O_5$) Calc'd.: C, 57.13; H, 6.05, N, 20.28. Found: C, 57.01; H, 5.99, N, 20.33.

Example 12

Preparation of 2',3'-O-isopropylidene-N⁶-((S)-α-phenylethyl-carbamoylamino)adenosine-5'-N-ethyluronamide Following the procedure outlined in Example 7, the title compound was prepared in an 82% yield as a white solid, mp 109–111° C. IR (KBr) $cm^{-1}$ 3445, 1725, 1615, 1560, 1230; $^1$H NMR (CDCl$_3$) δ: 0.85 (t, 3H, J=7); 1.40 (s, 3H); 1.63 (s, 3H); 1.64 (d, 3H, J=7); 3.00–3.09 (m, 2H); 4.72 (d, 1H, J=1.8); 5.17 (m, 1H); 5.39–5.50 (m, 2H); 6.14 (d, 1H, J=2); 6.57 (bs, 1H); 7.26–7.45 (m, 3H); 8.12 (s, 1H); 8.51 (s, 1H); 9.81 (bs, 1H); 10.87 (s, 1H). Anal. ($C_{23}H_{29}N_7O_5$) Calc'd.: C, 57.13; H, 6.05, N, 20.28. Found: C, 57.25; H, 6.11, N, 20.37.

Example 13

Preparation of 2',3'-O-isopropylidene-N⁶-(5-methyl-isoxazol-3-yl-carbamoylamino)adenosine-5'-N-ethyluronamide Following the procedure outlined in Example 7, the title compound was prepared in an 83% yield as a white solid, mp 120° C. IR (KBr) $cm^{-1}$ 3450, 1720, 1620, 1550, 1215; $^1$H NMR (CDCl$_3$) δ: 0.82 (t, 3H, J=7); 1.20 (s, 3H); 1.41 (s, 3H); 2.44 (s, 3H); 3.00–3.07 (m, 2H); 4.74 (d, 1H, J=2); 5.46–5.50 (m, 2H); 6.21 (d, 1H, J=2); 6.55 (t, 1H, J=2); 6.70 (s, 1H); 8.37 (s, 1H); 8.63 (s, 1H); 9.39 (bs, 1H); 12.34 (bs, 1H). Anal. ($C_{20}H_{24}N_8O_6$) Calc'd.: C, 50.84; H, 5.12, N, 23.72. Found: C, 50.96; H, 5.18, N, 23.64.

Example 14

Preparation of 2',3'-O-isopropylidene-N⁶-(1,3,4-thiadiazol-2-yl-carbamoylamino)adenosine-5'-N-ethyluronamide Following the procedure outlined in Example 7, the title compound was prepared in a 74% yield as a yellow solid, mp 148° C. IR (KBr) $cm^{-1}$ 3430, 1730, 1615, 1560, 1240; $^1$H NMR (CDCl$_3$) δ: 0.86 (t, 3H, J=7); 1.44 (s, 3H); 1.67 (s, 3H); 3.07–3.14 (m, 2H); 4.78 (d, 1H, J=1.8); 4.78 (d, 1H, J=1.8); 5.47–5.51 (m, 2H); 6.24 (d, 1H, J=1.8); 6.52 (t, 1H, J=2); 8.36 (s, 1H); 8.75 (s, 1H); 8.91 (bs, 1H), 9.40 (bs, 1H); 11.72 (bs, 1H). Anal. ($C_{18}H_{21}N_9O_5S$) Calc'd.: C, 45.47; H, 4.45, N, 26.51. Found: C, 45.39; H, 4.44, N, 26.46.

Example 15

Preparation of 2',3'-O-isopropylidene-N⁶-(4-n-propyloxy-phenylcarbamoylamino)adenosine-5'-N-ethyluronamide Following the procedure outlined in Example 7, the title compound was prepared in an 70% yield as a pale yellow foam. IR (neat) $cm^{-1}$ 3440, 1725, 1620, 1555, 1220; $^1$H NMR (CDCl$_3$) δ: 0.71 (t, 3H, J=7); 0.90 (s, 3H, J=7); 1.40 (s, 3H); 1.62 (s, 3H); 1.81–2.03 (m, 2H); 2.95–3.01 (m, 2H); 3.90 (t, 2H, J=7); 4.71 (d, 1H, J=1.8); 5.46–5.51 (m, 2H); 6.19 (d, 1H, J=1.8); 6.51 (t, 1H, J=2); 6.89 (d, 2H, J=9); 7.48

(d, 2H, J=9); 8.25 (s, 1H); 8.56 (s, 1H); 8.80 (bs, 1H), 11.48 (s, 1H). Anal. ($C_{22}H_{25}N_7O_5$) Calc'd.: C, 56.52; H, 5.39, N, 20.97. Found: C, 56.44; H, 5.42, N, 21.03.

Example 16

Preparation of 2',3'-O-isopropylidene-$N^6$-bis-(4-nitrophenyl-carbamoylamino)adenosine-5'-N-ethyluronamide Following the procedure outlined in Example 7, the title compound was prepared in an 65% yield as a yellow solid, mp 261° C. IR (KBr) cm$^{-1}$ 3430, 1730, 1620, 1555, 1210; $^1$H NMR (DMSO d6) δ: 0.56 (t, 3H, J=7); 1.34 (s, 3H); 1.54 (s, 3H); 2.67–2.83 (m, 2H); 4.61 (d, 1H, J=1.8); 5.47–5.50 (m, 2H); 6.47 (d, 1H, J=1.8); 7.61 (t, 1H, J=2); 7.71 (d, 2H, J=9); 7.91 (d, 2H, J=9); 8.22 (d, 2H, J=9); 8.24 (s, 1H), 8.64 (d, 2H, J=9); 9.72 (s, 1H); 10.63 (bs, 1H); 12.24 (s, 1H). Anal. ($C_{29}H_{28}N_{10}O_{10}$) Calc'd.: C,51.48; H, 4.17, N, 20.70. Found: C, 51.56; H, 4.16, N, 20.69.

Example 17

Preparation of 2',3'-O-isopropylidene-$N^6$-bis-(5-chloropyridin-2-yl-carbamoylamino)adenosine-5'-N-ethyluronamide Following the procedure outlined in Example 7, the title compound was prepared in a 60% yield as a yellow foam. IR (neat) cm$^{-1}$ 3440, 1710, 1630, 1540, 1220; $^1$H NMR (CDCl$_3$) δ: 0.58 (t, 3H, J=7); 1.35 (s, 3H); 1.54 (s, 3H); 2.71–2.85 (m, 2H); 4.60 (d, 1H, J=2); 5.47–5.51 (m, 2H); 6.47 (d, 1H, J=2); 7.52 (t, 1H, J=2); 7.79–7.92 (m, 4H); 8.34–8.38 (m, 2H); 8.60 (s, 1H); 8.65 (s, 1H), 10.66 (bs, 1H); 12.22 (bs, 1H). Anal. ($C_{27}H_{26}N_8O_6Cl_2$) Calc'd.: C, 51.52; H, 4.16, N, 17.80. Found: C, 51.55; H, 4.13, N, 17.84.

Example 18

General procedure for the preparation of $N^6$-(substituted)adenosine-5'-N-ethyluronamide A solution of the isopropylidene derivative (0.084 mmol) in aqueous 1N HCl (5 ml) and dioxane (5 ml) was stirred at 65° C. for 1 hour. The solvent was then removed under reduced pressure and the residue was crystallized from ethanol to afford the desired compounds.

Example 19

Preparation of $N^6$-(4-biphenyl-carbonylamino)-adenosine-5'-N-ethyluronamide

Following the procedure outlined in Example 18, the title compound was prepared in a 65% yield as a white solid, mp 221° C. IR (KBr) cm$^{-1}$ 3500–3100, 1720, 1615, 1550; $^1$H NMR (DMSO d$_6$) δ: 1.07 (t, 3H, J=7); 3.17–3.24 (m, 2H); 4.23–4.25 (m, 1H); 4.36 (d, 1H, J=2); 4.71–4.73 (m, 1H); 5.70 (d, 1H, J=8); 5.79 (d, 1H, J=4); 6.13 (d, 1H, J=8); 7.43–7.53 (m, 3H); 7.78–7.89 (m, 4H); 8.16 (d, 2H, J=11); 8.46 (t, 1H, J=4), 8.80 (s, 1H); 8.82 (s, 1H); 11.34 (bs, 1H). Anal. ($C_{25}H_{24}N_6O_5$) Calc'd C, 61.47; H, 4.95, N, 17.20. Found: C, 61.57; H, 5.00, N, 17.28.

Example 20

Preparation of $N^6$-(2,4-dichlorobenzyl-carbonylamino)-adenosine-5'-N-ethyluronamide Following the procedure outlined in Example 18, the title compound was prepared in a 55% yield as a white solid, mp 132–134° C. IR (KBr) cm$^{-1}$ 3450–3050, 1730, 1635, 1545, 1230; $^1$H NMR (DMSO d$_6$) δ: 1.08 (t, 3H, J=7); 3.18–3.25 (m, 2H); 3.34 (s, 2H); 4.12–4.15 (m, 1H); 4.30 (s, 1H); 4.49–4.62 (m, 2H); 5.57 (d, 1H, J=8); 5.77 (d, 1H, J=4); 5.95 (d, 1H, J=8); 7.44–7.51 (m, 3H); 8.19 (s, 1H); 8.39 (s, 1H), 8.95 (bs, 1H). Anal. ($C_{20}H_{20}N_6O_5$) Calc'd.: C, 56.60; H, 4.75, N, 19.80. Found: C, 56.60; H, 4.77, N, 19.84.

Example 21

Preparation of $N^6$-(4-methoxyphenyl-carbonylamino)-adenosine-5'-N-ethyluronamide Following the procedure outlined in Example 18, the title compound was prepared in an 80% yield as a white solid, mp 167–169° C. IR (KBr) cm$^{-1}$ 3550–3150, 1710, 1640, 1530, 1270; $^1$H NMR (DMSO d$_6$) δ: 1.07 (t, 3H, J=7); 3.15–3.23 (m, 2H); 3.86 (s, 3H); 4.20–4.24 (m, 1H); 4.35 (d, 1H, J=2); 4.70–4.75 (m, 1H); 5.69 (d, 1H, J=7); 5.77 (d, 1H, J=4); 6.11 (d, 1H, J=7); 7.08 (d, 2H, J=9); 8.04 (d, 2H, J=9); 8.44 (bs, 1H); 8.77 (s, 1H); 8.78 (s, 1H), 11.12 (s, 1H). Anal. ($C_{20}H_{22}N_6O_6$) Calc'd.: C, 54.30; H, 5.01, N, 18.99. Found: C, 54.38; H, 4.98, N, 19.02.

Example 22

Preparation of $N^6$-(4-chlorophenyl-carbonylamino)-adenosine-5'-N-ethyluronamide Following the procedure outlined in Example 18, the title compound was prepared in a 78% yield as a white solid, mp 179–180° C. IR (KBr) cm$^{-1}$ 3510–3050, 1720, 1660, 1510, 1250; $^1$H NMR (DMSO d$_6$) δ: 1.06 (t, 3H, J=7); 3.15–3.22 (m, 2H); 4.22 (bs, 1H); 4.34 (s, 1H); 4.68–4.70 (m, 1H); 5.66 (d, 1H, J=7); 5.76 (d, 1H, J=4); 6.10 (d, 1H, J=7); 7.43–7.61 (m, 4H); 8.44 (bs, 1H); 8.67 (s, 1H); 8.82 (bs, 1H); 11.53 (bs, 1H). Anal. ($C_{19}H_{19}N_6O_5$) Calc'd.: C, 55.47; H, 4.66, N, 20.43. Found: C, 55.53; H, 4.72, N, 20.50.

Example 23

Preparation of $N^6$-(phenyl-carbonylamino)-adenosine-5'-N-ethyluronamide

Following the procedure outlined in Example 18, the title compound was prepared in a 67% yield as a white solid, mp 157–159° C. IR (KBr) cm$^{-1}$ 3500–3000, 1715, 1630, 1535, 1260; $^1$H NMR (DMSO d$_6$) δ: 1.03 (t, 3H, J=7); 3.16–3.19 (m, 2H); 3.74 (bs, 1H); 4.22 (bs, 1H); 4.36 (s, 1H); 4.51–4.63 (m, 1H); 6.13 (d, 1H, J=6.8); 7.48–7.59 (m, 3H); 8.04–8.11 (m, 2H); 8.52 (bs, 1H), 8.79 (s, 1H); 8.83 (s, 1H); 11.22 (s, 1H). Anal. ($C_{19}H_{20}N_6O_5$) Calc'd.: C, 55.34; H, 4.89, N, 20.38. Found: C, 55.47; H, 4.93, N, 20.43.

Example 24

Preparation of $N^6$-(benzylcarbamoylamino)-adenosine-5'-N-ethyluronamide

Following the procedure outlined in Example 18, the title compound was prepared in a 70% yield as a white solid, mp 184–186° C. IR (KBr) cm$^{-1}$ 3500–3100, 1675, 1620, 1565, 1520, 1310; $^1$H NMR (DMSO d$_6$) δ: 1.06(t, 3H, J=7); 3.10–3.20 (m, 2H); 4.05 (bs, 1H); 4.17–4.20 (m, 1H); 4.36 (s, 1H); 4.47–4.50 (m, 2H); 4.55–4.65 (m, 1H); 6.05–6.10 (m, 1H); 7.17–7.40 (m, 5H); 8.30–8.40 (m, 1H); 8.62 (s, 1H); 8.86 (s, 1H); 9.50–9.60 (m, 1H); 10.30 (bs, 1H). Anal. ($C_{20}H_{24}N_7O_5$) Calc'd.: C, 54.29; H, 5.47, N, 22.16. Found: C, 54.36; H, 5.52, N, 22.08.

Example 25

Preparation of $N^6$-(4-sulfonamido-phenylcarbamoyl)-adenosine-5'-N-ethyluronamide Following the procedure outlined in Example 18, the title compound was prepared in a 63% yield as a white solid, mp 183–185° C. IR (KBr) cm$^{-1}$ 3550–3050, 1715, 1630, 1545, 1370, 1250; $^1$H NMR (DMSO d$_6$) δ: 1.07 (t, 3H, J=7); 3.16–3.26 (m, 2H); 4.21 (bs, 1H); 4.36 (s, 1H); 4.63–4.69 (m, 1H); 5.62 (d, 1H, J=6.8); 5.78 (d, 1H, J=4); 6.11 (d, 1H, J=6.8); 7.31 (bs, 2H); 7.81 (s, 4H); 8.49 (bs, 1H); 8.75 (s, 1H), 8.89 (s, 1H); 9.69 (bs, 1H); 11.92 (bs, 1H). Anal. (C$_{19}$H$_{22}$N$_8$O$_7$S) Calc'd.: C, 45.06; H, 4.38, N, 22.12. Found: C, 45.15; H, 4.36, N, 22.07.

Example 26

Preparation of N$^6$-(4-acetyl-phenylcarbamoyl)-adenosine-5'-N-ethyluronamide

Following the procedure outlined in Example 18, the title compound was prepared in an 83% yield as a white solid, mp 187° C. IR (KBr) cm$^{-1}$ 3550–3100, 1740, 1720, 1630, 1525, 1215; $^1$H NMR (DMSO d$_6$) δ: 1.08 (t, 3H, J=7); 2.55 (s, 2H); 3.16–3.23 (m, 2H); 4.18–4.20 (m, 1H); 4.21 (d, 1H, J=2); 4.45 (bs, 1H); 4.64–4.69 (m, 1H); 6.11 (d, 1H, J=7); 7.77 (d, 2H, J=9); 7.98 (d, 2H, J=9); 8.49 (bs, 1H), 8.76 (s, 1H); 8.88 (s, 1H); 10.62 (bs, 1H); 11.94 (bs, 1H). Anal. (C$_{21}$H$_{23}$N$_7$O$_6$) Calc'd.: C, 53.73; H, 4.94, N, 20.89. Found: C, 53.80; H, 4.95, N, 20.93.

Example 27

Preparation of N$^6$-((R)-α-phenylethylcarbamoyl)-adenosine-5'-N-ethyluronamide

Following the procedure outlined in Example 18, the title compound was prepared in a 65% yield as a white solid, mp 153–155° C. IR (KBr) cm$^{-1}$ 3550–3100, 1720, 1635, 1535, 1240; $^1$H NMR (DMSO d$_6$) δ: 1.05 (t,3H, J=7); 1.51 (d, 3H, J=8); 3.14–3.21 (m, 2H); 3.35–3.41 (m, 1H); 4.20 (s, 1H); 4.36 (s, 1H); 4.93–5.00 (m, 3H); 6.09 (d, 1H, J=6.8); 7.25–7.39 (m, 5H); 8.48 (bs, 1H); 8.65 (s, 1H); 8.89 (s, 1H); 9.51 (bs, 1H); 10.38 (bs, 1H). Anal. (C$_{21}$H$_{25}$N$_7$O$_5$) Calc'd.: C, 53.50; H, 5.34, N, 20.80. Found: C, 53.55; H, 5.38, N, 20.85.

Example 28

Preparation of N$^6$-((S)-α-phenylethylcarbamoyl)-adenosine-5'-N-ethyluronamide

Following the procedure outlined in Example 18, the title compound was prepared in a 72% yield as a white solid, mp 151° C. IR (KBr) cm$^{-1}$ 3550–3100, 1725, 1630, 1525, 1240; $^1$H NMR (DMSO d$_6$) δ: 1.06 (t, 3H, J=7); 1.49 (d, 3H, J=8); 3.15–3.21 (m, 2H); 3.28–3.39 (m, 1H); 4.00 (bs, 1H); 4.35 (s, 1H); 4.61–4.66 (m, 1H); 4.95–5.01 (m, 1H); 6.07 (d, 1H, J=6.8); 7.24–7.39 (m, 5H); 8.48 (bs, 1H), 8.64 (s, 1H); 8.83 (s, 1H); 9.57 (bs, 1H); 10.12 (bs, 1H). Anal. (C$_{21}$H$_{25}$N$_7$O$_5$) Calc'd.: C, 53.50; H, 5.34, N, 20.80. Found: C, 53.44; H, 5.34, N, 20.77.

Example 29

Preparation of N$^6$-(5-methyl-isoxazol-3-yl-carbamoyl)-adenosine-5'-N-ethyluronamide Following the procedure outlined in Example 18, the title compound was prepared in a 58% yield as a white solid, mp 197° C. IR (KBr) cm$^{-1}$ 3550–3050, 1715, 1620, 1535, 1240; $^1$H NMR (DMSO d$_6$) δ: 1.06 (t, 3H, J=7); 2.40 (s, 3H); 3.12–3.25 (m, 2H); 4.21–4.23 (m, 1H); 4.36 (d, 1H, J=2); 4.64–4.70 (m, 1H); 5.68 (m, 2H); 6.09 (d, 1H, J=6.8); 6.67 (s, 1H); 8.46 (t, 1H, J=6), 8.74 (s, 1H); 8.84 (s, 1H); 10.75 (bs, 1H); 12.19 (bs, 1H). Anal. (C$_{17}$H$_{20}$N$_8$O$_6$) Calc'd.: C, 47.22; H, 4.66, N, 25.91. Found: C, 47.14; H, 4.69, N, 25.96.

Example 30

Preparation of N$^6$-(1,3,4-thiadiazol-2-yl-carbamoyl)-adenosine-5'-N-ethyluronamide Following the procedure outlined in Example 18, the title compound was prepared in a 65% yield as a white solid, mp 197° C. IR (KBr) cm$^{-1}$ 3450–3100, 1720, 1635, 1515, 1240; $^1$H NMR (DMSO d$_6$) δ: 1.06 (t, 3H, J=7); 3.15–3.22 (m, 2H); 3.72 (bs, 2H); 4.21–4.24 (m, 1H); 4.36 (d, 1H, J=2); 4.65–4.70 (m, 1H); 6.12 (d, 1H, J=6.8); 8.45 (t, 1H, J=7); 8.80 (s, 1H); 8.89 (s, 1H); 9.19 (s, 1H); 10.35 (bs, 1H); 11.38 (bs, 1H). Anal. (C$_{15}$H$_{17}$N$_4$O$_5$S) Calc'd.: C, 49.31; H, 4.69, N, 15.33. Found: C, 49.22; H, 4.72, N, 15.33.

Example 31

Preparation of N$^6$-(4-n-propoxy-phenylcarbamoyl)-adenosine-5'-N-ethyluronamide Following the procedure outlined in Example 18, the title compound was prepared in a 66% yield as a white solid, mp 270° C. IR (KBr) cm$^{-1}$ 3450–3050, 1720, 1630, 1535, 1240; $^1$H NMR (DMSO d$_6$) δ: 0.95 (t, 3H, J=7); 1.09 (t, 3H, J=7); 1.65–1.75 (m, 2H); 3.06–3.23 (m, 2H); 3.67 (bs, 2H); 3.89 (t, 2H, J=7); 4.18–4.20 (m, 1H); 4.33 (s, 1H); 4.51–4.61 (m, 1H); 6.05 (d, 1H, J=6.8); 6.91 (d, 2H, J=9); 7.52 (d, 2H, J=9); 7.92 (t, 1H, J=7); 8.22 (s, 1H); 8.52 (s, 1H); 9.65 (bs, 1H); 11.52 (bs, 1H). Anal. (C$_{22}$H$_{27}$N$_7$O$_6$) Calc'd.: C, 5.61; H, 5.61, N, 20.19. Found: C, 54.50; H, 5.66, N, 20.06.

Example 32

Preparation of N$^6$-bis-(4-nitrophenylcarbamoyl)-adenosine-5'-N-ethyluronamide

Following the procedure outlined in Example 18, the title compound was prepared in a 52% yield as a white solid, mp 213° C. IR (KBr) cm$^{-1}$ 3500–3050, 1720, 1630, 1545, 1340, 1220; $^1$H NMR (DMSO d$_6$) δ: 1.07 (t, 3H, J=7); 3.12–3.23 (m, 2H); 4.21–4.23 (m, 1H); 4.35 (d, 1H, J=2); 4.64–4.69 (m, 1H); 5.69 (bs, 2H); 6.09 (d, 1H, J=6.8); 7.68 (d, 2H, J=9); 7.91 (d, 2H, J=9); 8.18–8.29 (m, 4H); 8.83 (s, 1H); 9.69 (s, 1H); 10.68 (bs, 1H); 12.26 (bs, 1H). Anal. (C$_{26}$H$_{29}$N$_{10}$O$_{10}$) Calc'd.: C, 48.67; H, 4.56, N, 21.83. Found: C, 48.74; H, 4.60, N, 21.88.

Example 33

Preparation of N$^6$-bis-(5-chloro-pyridin-2-yl-carbamoyl)-adenosine-5'-N-ethyluronamide Following the procedure outlined in Example 18, the title compound was prepared in a 68% yield as a white solid, mp 220° C. IR (KBr) cm$^{-1}$ 3550–3100, 1725, 1630, 1525, 1250; $^1$H NMR (DMSO d$_6$) δ: 1.06 (t, 3H, J=7); 3.15–3.22 (m, 2H); 4.22–4.24 (m, 1H); 4.36 (d, 2H, J=2); 4.64–4.69 (m, 1H); 5.95 (bs, 2H); 6.10 (d, 1H, J=6.8); 7.80–8.06 (m, 6H); 8.39 (t, 1H, J=7); 8.76 (s, 1H); 8.93 (s, 1H); 10.39 (bs, 1H); 12.11 (bs, 1H). Anal. (C$_{24}$H$_{22}$N$_8$O$_6$Cl$_2$) Calc'd.: C, 48.91; H, 3.76, N, 19.01. Found: C, 49.01; H, 3.77, N, 18.89.

Example 34

Binding Assays
Methods for Performing Receptor Binding Assays

Procedures for preparing rat brain membranes and Chinese hamster ovary (CHO) cell membranes were as reported[30, 38, 44]. For binding experiments, membrane homogenates were frozen and stored at −20° C. for greater than 2 months. Adenosine deaminase (ADA) was purchased from Boehringer Mannheim (Indianapolis, Ind.). [$^3$H]R-PIA was purchased from Amersham (Arlington Heights, Ill.), and [$^3$H]CGS 21680 was purchased from DuPont NEN (Boston, Mass.). [$^{125}$I]-AB-MECA was prepared as described by Olah et al.[30]

The binding of [$^{125}$I]-AB-MECA to CHO cells stably transfected with the rat $A_3$ receptor clone or to HEK-293 cells stably expressing the human $A_3$ receptor, was performed essentially as described[28, 30, 38, 44]. Assays were performed in 50 mM Tris/10 mM MgCl$_2$/1 mM EDTA buffer (adjusted to pH 8.26 at 5° C.) in glass tubes containing 100 µl of the membrane suspension, 50 µl of [$^{125}$I]-AB-MECA (final concentration 0.3 nM), and 50 µl of inhibitor. Inhibitors were routinely dissolved in DMSO. Concentrations of DMSO in incubations never exceeded 1%; this concentration did not influence [I$^{25}$I]-AB-MECA binding. Incubations were carried out in duplicate for 1 h at 37° C., and were terminated by rapid filtration over Whatman GF/B filters using a Brandell cell harvester (Brandell, Gaithersburg, Md.). Tubes were washed three times with 3 mL of buffer. Radioactivity was determined in a Beckman gamma 5500B γ-counter.

Nonspecific binding was determined in the presence of 200 µM NECA. $K_1$ values were calculated according to Cheng-Prusoff[45] assuming a $K_d$ for [$^{125}$I]-AB-MECA of 1.48 nM. Binding of [$^3$H]R-PIA to $A_1$ receptors from rat cortical membranes and of [$^3$H]CGS 21680 to $A_{2A}$ receptors for rat striatal membranes was performed as described previously.[46] Adenosine deaminase (2 units/mL) was present during the preparation of the membranes. Additional deaminase was not added during incubation with the radioligand.

Binding of [$^{35}$S]GTP-γ-S

The binding for [$^{35}$S]GTP-γ-S (Ameersham, Chicago Ill., specific activity 1275 Ci/mmol) was carried out using rat RBL-2H3 mast cell membranes by the general method of Lorenzen et al.[47] Membranes were suspended in a buffer containing 50 mM Tris, 3 units/mL adenosine deaminase, 100 mM NaCl, and 10 mM MgCl$_2$ (pH 7.4) and a protein concentration of 1 to 10 µg per tube. The membrane suspension was preincubated with 10 GDP, R-PIA and/or riboflavin in a final volume of 125 µL buffer at 30° C. for 60 min and then transferred to ice for 20 min. [$^{35}$S]GTP-γγ-S was added to a final concentration of 0.1 nM in a total volume of 500 µL and the mixture was incubated for 30 min at 30° C. Non-specific binding was determined in the presence of 10 µM GTP-γ-S (Sigma, St. Louis Mo.). Incubation of the reaction mixture was terminated by filtration over a GF/B glass filter using a Brandell cell harvester and washed with the same buffer.

Results and Discussion

The derivatives 3a-o (the compounds in Examples 19–33, sequentially) were tested in radioligand binding assays for affinity at rat brain $A_1$, $A_{2A}$ and $A_3$ receptors, and the results are summarized in Table 1.

TABLE 1

Affinities of N$^6$-Substituted-carbamoyl-adenosine-5'uronamide Derivatives in Radioligand Binding Assays at Rat Brain $A_1$, $A_{2A}$ and $A_3$ Adenosine Receptors

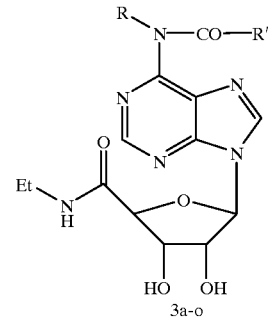

3a-o

| Compound | R | R' | $K_i$ $(A_1)^a$ | $K_i$ $(A_{2A})^b$ | $K_i$ $(A_3)^c$ | $A_1/A_3$ | $A_{2A}/A_3$ |
|---|---|---|---|---|---|---|---|
| IB-MECA 1 | — | — | 54 ± 5 | 56 ± 8 | 1.1 ± 0.3 | 49 | 51 |
| 3a | H | 4-Biphenyl | 5.92 ± 1.04 | 3580 ± 850 | 979 ± 22 | 0.006 | 3.65 |
| 3b | H | 2,4-Cl—Ph—CH$_2$ | 16 ± 3.3 | 26.6 ± 8.8 | 167 ± 7 | 0.095 | 0.16 |
| 3c | H | 4-CH$_3$O—Ph | 86.4 ± 14.2 | 237 ± 46 | 837 ± 142 | 0.10 | 0.28 |
| 3d | H | 2-Cl—Ph | 1170 ± 220 | 1960 ± 300 | 754 ± 132 | 1.55 | 2.59 |
| 3e | H | Ph | 252 ± 52 | 670 ± 211 | 824 ± 126 | 0.30 | 0.81 |
| 3f | H | Ph—CH$_2$—NH | 171 ± 15 | 1793 ± 230 | 38.3 ± 6.4 | 4.46 | 46.8 |
| 3g | H | 4-SO$_2$NH$_2$—Ph—NH | 453 ± 141 | 1180 ± 360 | 9.73 ± 0.75 | 46.5 | 121.2 |
| 3h | H | 4-CH$_3$CO—Ph—NH | 72.7 ± 11.8 | 1050 ± 270 | 20.9 ± 7.51 | 3.47 | 50.2 |
| 3i | H | (R)-α-Phenylethyl-NH | 433 ± 171 | 279 ± 171 | 16.3 ± 3.7 | 26.5 | 17.1 |
| 3j | H | (S)-α-Phenylethyl-NH | 537 ± 33 | 2970 ± 930 | 319 ± 134 | 1.68 | 9.3 |
| 3k | H | 5-Me-Isoxazol-3-yl-NH | 146 ± 39 | 884 ± 232 | 532 ± 240 | 0.27 | 1.66 |
| 3l | H | 1,3,4-Thiadiazol-2-yl-NH | 208 ± 42 | 917 ± 254 | 5550 ± 2800 | 0.037 | 0.16 |
| 3m | H | 4-nC$_3$H$_7$O—Ph—NH | 257 ± 43 | 255 ± 85 | 107 ± 34 | 2.3 | 2.4 |
| 3n | 4-NO$_2$—Ph—NH—CO | 4-NO$_2$—Ph—NH | 89.1 ± 8.8 | 2530 ± 200 | 168 ± 42 | 0.53 | 15 |

TABLE 1-continued

Affinities of N[6]-Substituted-carbamoyl-adenosine-5'uronamide Derivatives in Radioligand Binding Assays at Rat Brain $A_1$, $A_{2A}$ and $A_3$ Adenosine Receptors

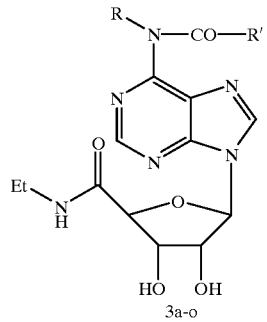

3a-o

| Compound | R | R' | $K_i$ $(A_1)$[a] | $K_i$ $(A_{2A})$[b] | $K_i$ $(A_3)$[c] | $A_1/A_3$ | $A_{2A}/A_3$ |
|---|---|---|---|---|---|---|---|
| 3o | 5-Cl—Pyridin-2-yl-NH—CO | 5-Cl-Pyridin-2-yl-NH | 761 ± 187 | 799 ± 191 | 5700 ± 100 | 0.13 | 0.14 |

[a]Displacement of specific [³H]R-PIA binding ($A_1$) in rat brain membranes, expressed as $K_i$ ± SEM in nM (n = 3–6).
[b]Displacement of specific [³H]CGS 21680 binding ($A_{2A}$) in rat striatal membranes expressed as $K_i$ ± SEM in nM (n = 3–6).
[c]Displacement of specific [¹²⁵IH]AB-MECA binding at rat $A_3$ receptors expressed in CHO cells, expressed as $K_i$ ± SEM in nM (n = 3–6).

Baraldi demonstrated that certain N[6]-substituted-arylcarbamoyl adenosine-uronamides are full agonists in inhibiting adenylate cyclase via rat $A_3$ receptors, but that the compounds showed relatively high activity with respect to adenosine $A_1$ receptors[39]. There is a similarity between $A_1$ and $A_3$ receptors. Small modifications in the length of chain at the N[6] position can alter the affinity versus $A_1$ or $A_3$ receptors. The present binding data demonstrate that the presence of aryl- or alkaryl-carbamoylic chains at the N[6]-position bring about an interaction with the $A_3$ receptor subtype. Also, the data demonstrate that heteroaryl-carbamoyl, heteroaryl-carboxamide, aryl-carboxamide, and alkaryl-carboxamide substitutions at the N[6]-position bring about an interaction with the $A_1$ receptor subtype.

In the series of urea-derivatives (Compounds 3f-o) a substituted-phenyl (Compounds 3g, h and m) or substituted-benzyl (Compounds 3f, i and j) group leads to relatively high affinity and selectivity at $A_3$ adenosine receptors as compared with the affinity for the $A_1$ and $A_2$ receptors.

Derivatives 3g, 3h and 3m showed a relatively high affinity (9.7–107 nM) at $A_3$ receptors with varying degrees of $A_3/A_1$ selectivity. In particular, compound 3g was less active than IB-MECA (9.7 nM vs. 1.1 nM) but showed selectivity for $A_3$ vs. either $A_1$ or $A_{2A}$ receptors which is comparable to IB-MECA.

Compound 3g also showed a relatively high affinity, in the nanomolar range, at human $A_3$ adenosine receptors (56.1±9.1 nM), confirming the relatively high affinity of this compound versus this receptor subtype, independent of species. The lipophilicity of para substituents on a phenyl ring play a significant role in $A_3$ affinity.

Substitution of the phenyl ring with a heterocycle (as in Compounds 3k-l) causes the compounds to lose affinity and selectivity for $A_3$ receptors, and increase in affinity for the $A_1$ receptor subtype.

Disubstitution at the N[6] position (for example, Compounds 3n-o) have diminished activity at $A_{2A}$ and $A_3$ receptors, but have relatively high affinity for the $A_1$ receptor.

In the benzylic series, Compounds 3f, i, and j showed an SAR pattern comparable to the phenylic series in Baraldi[39]. In fact, the unsubstituted Compound 3f showed affinity and selectivity at $A_3$ receptor very similar to the previously reported phenyl derivative.[39]

The stereochemistry of substituents at the N[6] position is also important in determining the affinity of these compounds for the $A_3$ receptor. For example, comparing the two diastereomeric Compounds 3i and 3j in which substituents at N[6] are of opposite configuration, the R-isomer (3i) is more potent and selective that the S-isomer (3j) at the rat $A_3$ adenosine receptor subtype. Those of skill in the art can separate compounds with stereocenters adjacent to the N[6] position using routine enantiopurification methods and evaluate the individual stereoisomers for their affinity and selectivity using no more than routine experimentation.

A functional assay indicated that Compound 3g acted as a full agonist at rat $A_3$ receptor. The assay involved the agonist-induced inhibition of binding of guanine nucleotide to rat RBL-2H3 mast cell membranes, which contain a high density of $A_3$ receptors.

FIG. 1 shows that compound 3g was about as effective as the potent $A_3$ agonists I-AB-MECA and Cl-IB-MECA increased binding of [³⁵S]GTP-γ-S in a dose dependent manner and with greater potency than NECA.

Example 35

Pharmaceutical Formulations (A) Transdermal System—for 1000 Patches

| Ingredients | Amount |
|---|---|
| Active compound | 100 g |
| Silicone fluid | 450 g |
| Colloidal silicon dioxide | 2 g |

The silicone fluid and active compound are mixed together and the colloidal silicon dioxide is added to increase viscosity. The material is then dosed into a subsequent heat sealed polymeric laminate including the following: polyester release liner, skin contact adhesive composed of silicone or acrylic polymers, a control membrane which is a polyolefin, and an impermeable backing membrane made of a polyester multilaminate. The resulting laminated sheet is then cut into 10 sq. cm patches (B) Oral Tablet—for 1000 Tablets

| Ingredients | Amount |
| --- | --- |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

(C) Injection—for 1000, 1 mL Ampules

| Ingredients | Amount |
| --- | --- |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

(D) Continuous Injection—for 1000 mL

| Ingredients | Amount |
| --- | --- |
| Active compound | 10 g |
| Buffering agents | q.s. |
| Water for injection | q.s. 1000 mL |

REFERENCES

The following references have been referred to herein. These references are incorporated herein by reference in their entirety.

1. Libert, F., Schiffmann, S. N.: Lefort, A., Parmentier, M; Gerard, C.; Dumont, J E.; Vanderhaeghen, J. J.; Vassart, G. The orphan receptor cDNA RDC7 encodes an $A_1$ adenosine receptor. *EMBO J.* 1991, 10, 1677–1682.
2. Maenhaut, C., Sande, J. V.; Libert, F; Abramowicz, M.; Parmentier, M.; Vanderhaeghen, J. J.; Dumont, J. E.; Vassart, G.; Schiffmann, S. RDC8 codes for an adenosine $A_2$ receptor with physiological constitutive activity. *Biochem. Biophys. Res. Commun.* 1990, 173, 1169–1178.
3. Stehle, J. H.; Rivkees, S. A.; Lee, J. J.; Weaver, D. R.; Deeds, J. D.; Reppert, S. M. Molecular cloning and expression of the cDNA for a novel $A_2$-adenosine receptor subtype. *Mol. Endocrinol.* 1992, 6, 384–393.
4. Zhou, Q. Y.; Li, C. Y.; Olah, M. E.; Johnson, R. A.; Stiles, G. L.; Civelli, O. Molecular cloning and characterization of an adenosine receptor- the $A_3$ adenosine receptor. *Proc. Natl. Acad. Sci. USA* 1992, 89, 7432–7436.
5. Londos, C., Cooper, D. M.; Wolff. J. Subclasses of external adenosine receptors. *Proc. Natl. Acad. Sci. USA* 1980, 77, 2551–2554.
6. Hamprecht, B.; Van Calker, D. Nomenclature of adenosine receptors. *Trends Pharmacol. Sci.* 1985,6, 153–154.
7. Ukena, D.; Olsson, R. A.; Daly, J. W. Definition of subclasses of adenosine receptors associated with adenylate cyclase: interaction of adenosine analogs with inhibitory $A_1$ receptors and stimulatory $A_2$ receptors. *Can. J. Physiol. Pharmacol.* 1987, 65. 365–376.
8. Ramkumar, V.; Stiles, G. L.; Beaven, M. A.; Ali, H. The $A_3AR$ is the unique adenosine receptor which facilitates release of allergic mediators in mast cells. *J Biol. Chem.*1993, 268, 6871–6890.
9. Abbracchio, M. P.; Brambilla, R.; Ceruti, S.: Kim, H. O.; von Lubitz, D. K. J. E.; Jacobson, K. A., Cattabeni, F. G-protein-dependent activation of phospholipase C by adenosine $A_3$ receptors in rat brain. *Mol. Pharmacol.* 1995, 48, 1038–1045.
10. Bruns, R. F.; Daly, J. W.; Snyder, S. H. Adenosine receptors in brain membranes: binding of N-cyclohexyl [$^3$H]adenosine and 1,3-diethyl-8($^3$H]phenylxanthine. *Proc. Natl. Acad. Sci. USA* 1980, 77, 5547–5551.
11. Olsson, R. A.; Kusachi, S.; Thompson, S. D.; Ukena, D., Padgett, W.; Daly, J. W. $N6^-$substituted N-alkyladenosine-$5^1$-uronamides: bifunctional ligands having recognition groups for $A_1$ and $A_2$ adenosine receptors. *J. Med. Chem.* 1986, 29, 1683–1689.
12. Jacobson, K. A.; Nikodijevic, O.; Ji, X. D.; Berkich, D. A.; Eveleth, D.; Dean, R. L.; Hiramatsu, K.; Kassel, N. F.; van Galen, P. J. M.; Lee, K. S.; Bartus, R. T.; Daly, J. W.; Lanoue, K. F.; Maillard, M. Synthesis and biological activity of $N^6$-(p-sulfophenyl)alkyl and $N^6$-p-sulfoalkyl derivatives of adenosine. Water soluble and peripherally selective adenosine agonists. *J. Med. Chem.* 1992, 35, 4143–4149.
13. Shamim, M. T.; Ukena, D.; Padgett, W. L.; Hong, O.; Daly, J. W. 8-Aryl- and 8cycloalkyl-1,3-dipropylxanthines: further potent and selective antagonists for $A_1$-adenosine receptors. *J. Med. Chem.* 1988, 31, 613–617.
14. Linden, J.; Patel, A.; Earl, C. Q.; Craig, R. H.; Daluge, S. M. ($^{125}$I]-labeled 8-phenylxanthine derivatives: antagonist radioligands for adenosine $A_1$ receptors. *J. Med. Chem.* 1988, 31, 745–751.
15. Jacobson, K. A. de la Cruz., R.; Schulick, R.; Kiriasis, K. L.; Padgett, W.; Pfleiderer, W.; Kirk, K. L.; Neumeyer, J. L., Daly, J. W. 8-substituted xanthines as antagonists at $A_1$ and $A_2$ adenosine receptors. *Biochem. Pharmacol.* 1988, 37, 3653–3661.
16. Cristalli, G.; Eleuteri, A.; Vittori, S.; Volpini, R.; Lohse, M. J.; Klotz, K. N. 2-alkynyl derivatives of adenosine and adenosine-5'-N-ethyluronamide as selective agonists at $A_2$ adenosine receptors. *J. Med. Chem.* 1992, 35, 2363–2368.
17. Jarvis, M. F.; Schulz, R.; Hutchison, A. J.; Do, U. H.; Sills, M. A.; Williams, M. [$^3$H]CGS 21680, a selective $A_2$ adenosine receptor agonist directly labels $A_2$ receptors in rat brain. *J. Pharmacol. Exp. Ther.* 1989, 251, 888–893.
18. Shimada, J.; Suzuki, K.; Nonaka, H.; [shii, A.; [chikawa, S. (E)-1,3-dialkyl-7-methyl-8-(3,4,5'-trimethoxystyryl) xanthines: potent and selective adenosine $A_2$ antagonists. *J. Med. Chem.* 1992, 35, 2342–2345.
19. a) Jacobson, K. A.; Gallo-Rodriguez, C.; Melman, N.; Fischer, B.; Malillard, M.; van Bergen, A.; van Galen, P. J. M.; Kar-ton, Y. Structure-activity relationship of 8-styrylxanthines as $A_2$-selective adenosine antagonists. *J. Med. Chem.* 1993, 36, 1333–1342; b) Baraldi, P. G.; Manfredini, S.; Simoni, D.; Zappaterra, L.; Zocchi, C.; Dionisotti, S.; Ongini, E. Synthesis and activity of new pyrazolo[4,3-e]-1,2,4-triazolo[1,5-c] pyrimidine and 1,2,3-triazolo[4,5-e] 1,2,4-triazolo [1,5-c]pyrimidine displaying potent and selective activity as $A_{2A}$ adenosine receptor antagonist. *Bioorg. Med. Chem. Lett.* 1994, 4, 2539–2544; c) Baraldi, P. G.; Cacciari, B.; Spalluto, G.; Borioni, A.; Viziano, M.; Dionisotti, S.; Ongini, E. Current developments of $A_{2A}$ adenosine receptor antagonists-*Current Medicinal Chemistry* 1995, 2, 707–722.

20. Ferré, S.; O'Connor, W. T.; Snaprud, P.; Ungerstedt, U.; Fuxe, K. Antagonistic interactions between adenosine $A_{2A}$ receptors and dopamine $D_2$ receptors in the ventral striopallidal system-implications for the treatment of schizophrenia. *Neurosci,* 1994. 63, 765–773.

21. Schingnitz, G.; Kufner-Mühl, U.; Ensinger, H.; Lehr, E.; Kuhn, F. J. Selective $A_1$-antagonists for treatment of cognitive deficits. *Nucleosides Nucleotides* 1991, 10, 1067–1076.

22. Bridges, A. J.; Moos, W. H.; Szotek, D. L.; Trivedi, B. K.; Bristol, J. A.; Heffner, T. G.; Bruns, R. F.; Downs, D. A. $N^6$-(2,2-diphenylethyl)adenosine, a novel adenosine receptor agonist with anti psychotic-like activity. *J. Med. Chem.* 1987, 30, 1709–1711.

23. Jacobson, K. A.: Tnivedi, B. K.; Churchill, P. C.; Williams, M. Novel therapeutics acting via purine receptors. *Biochem. Pharmacol.* 1991, 41, 1399–1410.

24. Jacobson, K. A.; Kim, H. O.: Siddiqi, S. M.; Olah, M. E.; Stiles, G.; von. Lubitz, D. K. J. $A_3$ adenosine receptors: design of selective ligands and therapeutic prospects. *Drugs Future* 1995, 20, 689–699.

25. Ji, X. D.; Melman, N.; Jacobson, K. A. Interactions of flavonoids and other phytochemicals with adenosine receptors. *J. Med. Chem.* 1996, 39, 781–788.

26. Karton, Y.; Jiang, J.-I.; Ji, X. D.; Melman, N.; Olah, M. E.; Stiles, G. L.; Jacobson, K. A. Synthesis and biological activities of flavonoid derivatives as $A_3$ adenosine receptor antagonists. *J. Med. Chem.* 1996, 39, 2293–2301.

27. van Rhee, A. M.; Jiang, J.-I.; Melman, N.; Olah, M. E.; Stiles, G. L.; Jacobson, K. A. Interaction of 1,4-dihydropyridine and pyridine derivatives with adenosine receptors: selectivity for $A_3$ receptors. *J. Med. Chem.* 1996, 39, 2980–2989.

28. Kim, Y.-C., Ji, X. D.; Jacobson, K. A. Derivatives of the triazoloquinazoline adenosine antagonist (CGS 15943) are selective for the human $A_3$ receptor subtype. *J. Med. Chem.* 1996, 39, 4142–4148.

29. Kim, H. O.; Ji, X. D.; Siddiqi, S. M.; Olah, M. E.; Stiles, G. L.; Jacobson, K. A. 2-substitution of $N^6$-benzyladenosine-5'-uronamides enhances selectivity for $A_3$ adenosine receptors. *J. Med. Chem.* 1994, 37, 3614–3621.

30. Olah, M. E.; Gallo-Rodriguez, C.; Jacobson, K. A.; Stiles, G. L. [$^{125}$I]AB-MECA, a high affinity radioligand for the rat $A_3$ adenosine receptor. *Mol. Pharmacol.* 1994, 45, 978–982.

31. Linden, J. Cloned adenosine $A_3$ receptors-pharmacological properties, species, differences and receptor functions. *Trends Pharmacol. Sci.* 1994, 15, 298–300.

32. Hannon, J. P.; Pfannkuche, H. J.; Fozard, J. R. A role for mast cells in adenosine $A_3$ receptor-mediated hypotension in the rat. *Br. J. Pharmacol.* 1995, 115, 945–952.

33. Fozard, J. R.; Pfannkuche, H. J.; Schuurmari, H. J. Mast cell degranulation following adenosine $A_3$ receptor activation in rats. *Eur. J. Pharmacol.* 1996, 298, 293–297.

34. Jacobson, K. A.; Nikodijevic, O.; Shi, D.; Gallo-Rodriguez, C.; Olah, M. E.; Stiles, G. L.; Daly, J. W. A role for central $A_3$-adenosine receptors: Mediation of behavioral depressant effects. *FEBS Lett* 1993, 336, 57–60.

35. von Lubitz, D. K. J. E.; Lin, R. C. S.; Popik, P.; Carter, M. F.; Jacobson, K. A. Adenosine $A_3$ receptor stimulation and cerebral ischemia *Eur. J. Pharmacol.* 1994, 263, 59–67.

36. Kohno, Y.; Sei, Y.; Koshiba, M.; Kim, H. O.; Jacobson, K. A. Induction of apoptosis in HL-60 human promyelocytic leukemia cells by selective adenosine $A_3$ receptor agonists. *Biochem. Biophys. Res. Commun.* 1996, 219, 904–910.

37. Jacobson, K. A.; van Galen, P. J. M.; Williams, M. Perspective Adenosine Receptors: pharmacology, structure-activity relationship and therapeutic potential. *J. Med. Chem.* 1992,35, 407–422.

38. Gallo-Rodriguez, C.; Ji, X. D.; Melman, N.; Siegman, B. D.; Sanders, L. H.; Orlina, J.; Pu, Q. L.; Olah, M. E.; van Galen, P. J. M.; Stiles, G. L.; Jacobson, K. A. Structure-activity relationship of $N^6$-benzyladenosine-5'-uronamides as $A_3$-selective adenosine agonists. *J. Med. Chem.* 1994, 37, 636–646.

39. Baraldi, P. G.; Cacciari, B.; Spalluto, G.; Ji, X. D.; Olah, M. E.; Stiles, G.; Dionisotti, S.; Zocchi, S.; Ongini, E.; Jacobson, K. A. Novel $N^6$-(substituted-phenylcarbamoyl) adenosine-5'-uronamides as potent agonists for $A_3$ adenosine receptors. *J. Med. Chem.* 1996, 39, 802–806.

40. Kurita, K.; Iwak-ura, Y. Trichloromethyl-Chloroformate as a phosgene equivalent: 3-isocyanatopropanoylchloride. *Org. Synth. Coll.*vol. VI, 1988, 715–718.

41. Siddiqi, S. M.; Pearlstein, R. A.; Sanders, L. H.; Jacobson, K. A. Comparative molecular field analysis of selective $A_3$ adenosine receptor agonists. *Bioorg. Med. Chem.* 1995, 3, 1331–1343.

42. van Galen, P. J. M.; Stiles, G. L.; Michaels, G.; Jacobson, K. A. Adenosine $A_1$ and $A_2$ receptors: structure-function relationships. *Med. Res. Rev.* 1992, 12, 423–471.

43. Muller, C. E.; Scior, T. Adenosine receptors and their modulators. *Pharmaceutica Acta Helviticae* 1993,68, 77–111.

44. van Galen, P. J. M.; van Bergen, A. H.; Gallo-Rodriguez, C.; Melman, N.: Olah, M. E.; Ijzerman, A. P.; Stiles, G. L.; Jacobson, K. A. A binding site model and structure-activity relationship for the rat $A_3$ adenosine receptor. *Mol. Pharmacol.* 1994, 45, 1101–1111.

45. Cheng, Y. C.; Prusoff, H. R. Relationships between the inhibition constant (Ki) and the concentration of inhibitor which causes 50% inhibition ($IC_{50}$) of an enzymatic reaction. *Biochem. Pharmacol.* 1973, 22, 3099–3108.

46. van Bergen, A.; van Galen, P. J. M., Stiles, G. L.; Jacobson, K. A. $A_3$ receptors: Structure activity relationship and molecular modeling. *ACS 206th National Meeting.* Chicago, Ill., August 1993, Abstract MED1217.

47. Lorenzen, A.; Guerra, L.; Vogt, H.; Schwabe, U. Interaction of full and partial agonists of the $A_1$ adenosine receptor with receptor/G protein complexes in rat brain membranes. *Mol. Pharmacol.* 1996, 49, 915–926.

Those skilled in the art will recognize, or be able to ascertain using no more than routine experimentation, many equivalents to the specific embodiments of the invention described herein. Such equivalents are intended to be encompassed by the following claims.

What is claimed is:
1. A compound of the following formula:

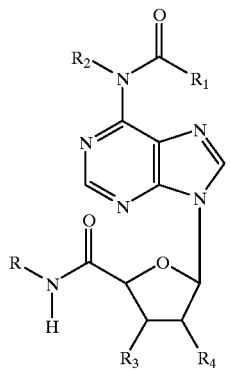

wherein:
R is hydrogen, alkyl, substituted alkyl, or aryl;
R¹ is heteroaryl-NR—, heteroaryl-, or aryl-,
R² is hydrogen, alkyl, substituted alkyl, or aryl-NH—C(X)—,
R³ and R⁴ are independently selected from the group consisting of hydroxy, hydrogen, halo, azido, alkyl, alkoxy, carboxy, cyano, nitro, aryl, and amino,
wherein the heteroaryl groups are selected from the group consisting of furyl, indolizinyl, benzothienyl, isoxazolyl, thiadiazolyl, and pyridinyl;
wherein the aryl groups may optionally be substituted with from 1 to 5 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, aryl, aryloxy, azido, carboxyl, carboxylalkyl, cyano, halo, nitro, heteroaryl, heteroaryloxy, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl,
wherein the heteroaryl groups may optionally be substituted with from 1 to 5 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, aryl, aryloxy, azido, carboxyl, carboxylalkyl, cyano, halo, nitro, heteroaryl, heteroaryloxy, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl, and trihalomethyl, and
X is O.
2. The compound of claim 1 wherein R is hydrogen.
3. The compound of claim 1 wherein R¹ is aryl-.
4. The compound of claim 1 wherein R¹ is heteroaryl-NR—.
5. The compound of claim 1 wherein R¹ is heteroaryl-.
6. A compound selected from the group consisting of:
N⁶-(4-biphenyl-carbonylamino)-adenosine-5'-N-ethyluronamide,
N⁶-(2,4-dichlorobenzyl-carbonylamino)-adenosine-5'-N-ethyluronamide,
N⁶-(4-methoxyphenyl-carbonylamino)-adenosine-5'-N-ethyluronamide,
N⁶-(4-chlorophenyl-carbonylamino)-adenosine-5'-N-ethyluronamide,
N⁶-(phenyl-carbonylamino)-adenosine-5'-N-ethyluronamide,
N⁶-(4-sulfonamido-phenylcarbamoylamino)-adenosine-5'-N-ethyluronamide,
N⁶-(4-acetyl-phenylcarbamoylamino)-adenosine-5'-N-ethyluronamide,
N⁶-((R)-α-phenylethylcarbamoylamino)-adenosine-5'-N-ethyluronamide,
N⁶-((S)-α-phenylethylcarbamoylamino)-adenosine-5'-N-ethyluronamide,
N⁶-(5-methyl-isoxazol-3-yl-carbamoylamino)-adenosine-5'-N-ethyluronamide,
N⁶-(1,3,4-thiadiazol-2-yl-carbamoylamino)-adenosine-5'-N-ethyluronamide,
N⁶-bis-(4-nitrophenylcarbamoylamino)-adenosine-5'-N-ethyluronamide, and
N⁶-bis-(5-chloro-pyridin-2-yl-carbamoylamino)-adenosine-5'-N-ethyluronamide.
7. A method of treating hypertension, or cardiac hypoxia, or providing protection against cerebral ischemia, comprising administering to a patient in need of treatment or protection thereof an effective amount of a compound of claim 1 which is an agonist or partial agonist of the A₃ receptor.
8. The method of claim 7 wherein R is hydrogen.
9. The method of claim 7 wherein R² is hydrogen.
10. A method of treating hypertension or cardiac hypoxia, or providing protection against cerebral ischemia, comprising administering to a patient in need of treatment or protection thereof an effective amount of a compound which is an agonist or partial agonist of the A₃ receptor, wherein the compound is selected from the group consisting of:
N⁶-(benzylcarbamoylamino)-adenosine-5'-N-ethyluronamide,
N⁶-(4-sulfonamido-phenylcarbamoylamino)-adenosine-5'-N-ethyluronamide,
N⁶-(4-acetyl-phenylcarbamoylamino)-adenosine-5'-N-ethyluronamide,
N⁶-((R)-α-phenylethylcarbamoylamino)-adenosine-5'-N-ethyluronamide,
N⁶-((S)-α-phenylethylcarbamoylamino)-adenosine-5'-N-ethyluronamide, and
N⁶-bis-(4-nitrophenylcarbamoylamino)-adenosine-5'-N-ethyluronamide.
11. A method for providing cardioprotection, neuroprotection, pain management, treatment of adenosine-sensitive cardiac arrythmias, treatment of convulsion, treatment of glaucoma; treatment of sleep apnea; treatment of paroxysmal supraventricular tachycardia, protection against hypoxia or protection against ischemia induced injuries comprising administering to a patient in need of treatment thereof an effective amount of a compound of the following formula:

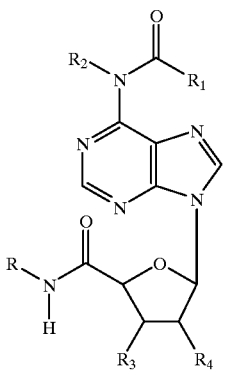

wherein:

R is hydrogen, alkyl, substituted alkyl or aryl;

$R^1$ is heteroaryl-NR—, heteroaryl-, or aryl-, $R^2$ is hydrogen, alkyl, substituted alkyl or aryl-NH—C(X)—, $R^3$ and $R^4$ are independently selected from the group consisting of hydroxy, hydrogen, halo, azido, alkyl, alkoxy, carboxy, cyano, nitro, aryl, and amino, wherein the heteroaryl groups are selected from the group consisting of furyl, indolizinyl, benzothienyl, isoxazolyl, thiadiazolyl, and pyridinyl;

wherein the aryl groups may optionally be substituted with from 1 to 5 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, aryl, aryloxy, azido, carboxyl, carboxylalkyl, cyano, halo, nitro, heteroaryl, heteroaryloxy, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl, wherein the heteroaryl groups may optionally be substituted with from 1 to 5 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, acyloxy, acylamino, aryl, aryloxy, azido, carboxyl, carboxylalkyl, cyano, halo, nitro, heteroaryl, heteroaryloxy, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl, and X is O, which is active as an agonist or partial agonist of the $A_1$ receptor.

12. The method of claim 11 wherein $R^1$ is aryl-.

13. The method of claim 11 wherein $R^1$ is heteroaryl-NR—.

14. The method of claim 11 wherein $R^1$ is heteroaryl-.

15. A method for providing cardioprotection, neuroprotection, pain management, treatment of adenosine-sensitive cardiac arrhythmias, treatment of convulsion, treatment of glaucoma; treatment of sleep apnea; treatment of peroxysmal supraventricular tachycardia, protection against hypoxia or protection against ischemia induced injuries comprising administering to a patient in need of treatment thereof an effective amount of a compound selected from the group consisting of:

$N^6$-(4-biphenyl-carbonylamino)-adenosine-5'-N-ethyluronamide, $N^6$-(2,4-dichlorobenzyl-carbonylamino)-adenosine-5'-N-ethyluronamide, $N^6$-(4-methoxyphenyl-carbonylamino)-adenosine-5'-N-ethyluronamide, $N^6$-(4-chlorophenyl-carbonylamino)-adenosine-5'-N-ethyluronamide, $N^6$-(phenyl-carbonylamino)-adenosine-5'-N-ethyluronamide, $N^6$-(5-methyl-isoxazol-3-yl-carbomayolamino)-adenoise-5'-N-ethyluromadine, $N^6$-91,3,4-thiadiazol-2-yl-carbamoylamino)-adenoise-5'-N-ethyluromadine, and $N^6$-(5-chloro-pyridin-2-yl-carbamoulamino)-adenoise-5'-N-ethyluromadine.

* * * * *